United States Patent
Tamagawa et al.

(10) Patent No.: US 9,288,986 B2
(45) Date of Patent: Mar. 22, 2016

(54) PLANT DISEASE CONTROL COMPOSITION AND METHOD FOR CONTROLLING PLANT DISEASE BY APPLYING THE SAME

(75) Inventors: Yasushi Tamagawa, Moriyama (JP); Hiroshi Ishimoto, Nagareyama (JP); Mayumi Takagi, Setagaya-ku (JP); Toshiaki Ohara, Moriyama (JP); Harukazu Tanaka, Hikone (JP)

(73) Assignee: MITSUI CHEMICALS AGRO, INC., Tokyo (JP)

( * ) Notice: Subject to any disclaimer, the term of this patent is extended or adjusted under 35 U.S.C. 154(b) by 0 days.

(21) Appl. No.: 13/518,136

(22) PCT Filed: Dec. 22, 2009

(86) PCT No.: PCT/JP2009/071287
§ 371 (c)(1),
(2), (4) Date: Jun. 21, 2012

(87) PCT Pub. No.: WO2011/077514
PCT Pub. Date: Jun. 30, 2011

(65) Prior Publication Data
US 2012/0282349 A1   Nov. 8, 2012

(51) Int. Cl.
| | | |
|---|---|---|
| A01N 43/42 | (2006.01) |
| A01N 37/20 | (2006.01) |
| A01N 37/24 | (2006.01) |
| A01N 37/38 | (2006.01) |
| A01N 37/42 | (2006.01) |
| A01N 37/52 | (2006.01) |
| A01N 43/32 | (2006.01) |
| A01N 43/40 | (2006.01) |
| A01N 43/56 | (2006.01) |
| A01N 43/78 | (2006.01) |
| A01N 43/80 | (2006.01) |
| A01N 47/02 | (2006.01) |

(52) U.S. Cl.
CPC ...................................... A01N 43/42 (2013.01)

(58) Field of Classification Search
USPC .......................................... 514/307, 406, 617
See application file for complete search history.

(56) References Cited

U.S. PATENT DOCUMENTS

2008/0275242 A1   11/2008  Ito et al.
2009/0325998 A1   12/2009  Ito et al.

FOREIGN PATENT DOCUMENTS

| | | | |
|---|---|---|---|
| JP | 2007-001944 A | 1/2007 |
| JP | 2007-217353 A | 8/2007 |
| WO | WO 2004/016088 | * | 2/2004 |
| WO | WO 2005/070917 A1 | 8/2005 |
| WO | WO 2007/011022 A1 | 1/2007 |
| WO | WO 2008/066148 A1 | 6/2008 |

OTHER PUBLICATIONS

Motoba, K. et al., "Mode of antifungal action and selectivity of Flutolanil," Agricultural and Biological Chemistry, vol. 52(6), pp. 1445-1449, 1988.*
Rummens, F.H.A., "An improved definition of synergistic and antagonistic effects," Weed Science, vol. 23 (1), pp. 4-6 (1975).*
Colby, S.R., "Calculating synergistic and antagonistic responses of herbicide combinations," Weeds, vol. 15, pp. 20-22 (1967).*
Richer, David L., "Synergism—a patent view," Pesticide Science, vol. 19 (4), pp. 309-315 (1987).*
HCAPLUS abstract 2003:175116 (2003).*
International Search Report (PCT/ISA/210) issued on Feb. 9, 2010, by the Japanese Patent Office as the International Searching Authority for International Application No. PCT/JP2009/071287.
Notification of Transmittal of Translation of the International Preliminary Report on Patentability (Chapter I and II) (Form PCT/IB/373 & Form PCT/IB/338) and the Written Opinion of the International Searching Authority (Form PCT/ISA/237) issued on Jul. 12, 2012, in the corresponding International Application No. PCT/JP2009/071287. (9 pages).

* cited by examiner

Primary Examiner — John Pak
(74) Attorney, Agent, or Firm — Buchanan, Ingersoll & Rooney PC

(57) ABSTRACT

This is to provide a plant disease control composition having a broad spectrum against various plant pathogens, and shows excellent controlling effects (synergistic controlling effects) which cannot be expected from a single component alone.

A plant disease control composition comprising (Group a) at least one quinoline compound represented by the formula:

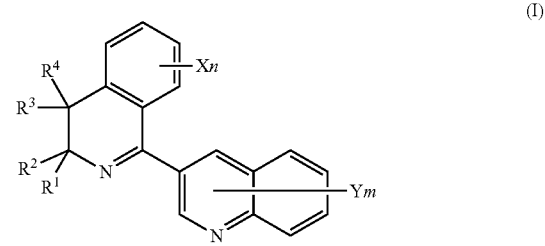

(I)

(wherein $R^1$, $R^2$: an alkyl which may be substituted, an aryl which may be substituted, etc.; $R^3$, $R^4$: H, an alkyl which may be substituted, etc.; X: halogen, an alkyl which may be substituted, etc.; Y: halogen, alkyl, etc.; n: 0 to 4; m: 0 to 6) or a salt thereof, and at least one of fungicidal compounds selected from the group consisting of a Strobilurin series compound, a triazole series compound, etc., as effective ingredients.

3 Claims, No Drawings

PLANT DISEASE CONTROL COMPOSITION AND METHOD FOR CONTROLLING PLANT DISEASE BY APPLYING THE SAME

TECHNICAL FIELD

The present invention relates to a plant disease control composition which comprises (Group a) at least one quinoline compound represented by the formula (I) or a salt thereof and (Group b) at least one fungicidal compound selected from the group consisting of Group 1 (b-1) to 28 (b-28) as effective ingredients and a method for controlling plant diseases by applying the composition.

BACKGROUND ART

A number of chemical agents have heretofore been used for controlling plant diseases. However, the problem that plant pathogens have acquired resistance to the chemical agents becomes remarkable due to frequent use or excessive application, etc., of the chemical agents having similar structures and same functions for controlling the same kinds of diseases.

On the other hand, consumers' needs for agricultural chemical-reduced crops and social needs to reduce environmental loads due to agricultural chemicals have now increased.

Also, in a farmer's field where the chemicals have been actually used, when two or more kinds of chemicals are used in admixture for the treatment by the tank mix method, there are many risks to lower the effect of the other chemical to be mixed with each other or possibilities to cause chemical damages against plant materials depending on a combination of chemicals where they are not well-suited to each other.

Under such a situation, it has been desired to develop a plant disease control composition having high effects against fungi or bacteria which are resistant to existing chemicals, and having high effects with a low amount of an effective ingredient. Moreover, for the purpose of preventing plant pathogens from obtaining resistance, it has also been desired to develop a plant disease control composition comprising components (compounds) having different basic structures and different functions with well-suited to each other, and a method for controlling plant diseases.

It has been known that a quinoline compound represented by the formula (I) shows, as a fungicide, controlling effects to rice blast (*Pyricularia oryzae*) and gray mold (*Botrytis cinerea*) of tomato, cucumber and kidney bean, etc., by an application method such as seed disinfection, foliar spray treatment, etc. (Patent Literatures 1 to 4).

However, it has never been known yet about a controlling effect of the quinoline compound represented by the formula (I) and the other fungicide(s) in admixture.
[Patent Literature 1] WO 2005/070917A
[Patent Literature 2] JP 2007-1944A
[Patent Literature 3] WO 2007/011022A
[Patent Literature 4] JP 2007-217353A

DISCLOSURE OF THE INVENTION

Problems to be Solved by the Invention

The present inventors have investigated a combination of the quinoline compound represented by the formula (I) and the other fungicidal component(s), and as a result, they have found that by combining the quinoline compound represented by the formula (I) and a specific fungicidal compound(s), excellent controlling effects (synergistic effects) against various plant pathogens can be obtained, which could never be expected from the single component alone, stable prophylaxis effect can be obtained against the existing fungi and bacteria resistant to chemicals, and no chemical damage to plants occurred to accomplish the present invention.

An object of the present invention is to provide a novel plant disease control composition having a broad spectrum against various kinds of plant pathogens, having high plant disease controlling effects against existing fungi and bacteria resistant to chemicals, showing high activity even when amounts of effective ingredients to be applied to environment where fungi or bacteria are living are low, and showing no chemical damage against plants, and a method for controlling plant disease by applying the composition.

Means to Solve the Problems

The present invention comprises a plant disease control composition containing (Group a)
(a) at least one kind of a quinoline compound represented by the general formula (I):

[Formula 1]

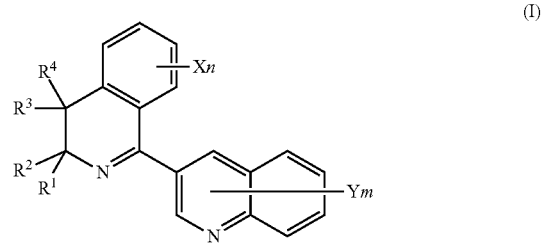

(I)

[wherein $R^1$ and $R^2$ may be the same or different from each other, and each represents a $C_1$ to $C_6$ alkyl group which may be substituted by the same or different 1 to 3 substituent(s) selected from the group consisting of a halogen atom, a $C_1$ to $C_6$ alkoxyl group, a $C_1$ to $C_6$ alkylthio group and a phenoxy group;

an aryl group which may be substituted by the same or different 1 to 6 substituent(s) selected from the group consisting of a halogen atom, a $C_1$ to $C_6$ alkyl group which may be substituted by the same or different 1 to 3 halogen atom(s), a $C_1$ to $C_6$ alkoxyl group, an amino group which may be substituted by the same or different 1 or 2 $C_1$ to $C_6$ alkyl group(s) or acyl group(s), a nitro group, a cyano group, a hydroxyl group, a mercapto group and a $C_1$ to $C_6$ alkylthio group;

a heteroaryl group which may be substituted by the same or different 1 to 6 substituent(s) selected from the group consisting of a halogen atom, a $C_1$ to $C_6$ alkyl group which may be substituted by the same or different 1 to 3 halogen atom(s) and a $C_1$ to $C_6$ alkoxyl group; or an aralkyl group which may be substituted by the same or different 1 to 6 substituent(s) selected from the group consisting of a halogen atom, a $C_1$ to $C_6$ alkyl group which may be substituted by the same or different 1 to 3 halogen atom(s), a $C_1$ to $C_6$ alkoxyl group, an amino group which may be substituted by the same or different 1 or 2 $C_1$ to $C_6$ alkyl group(s) or acyl group(s), a nitro group, a cyano group, a hydroxyl group, a mercapto group and a $C_1$ to $C_6$ alkylthio group, or, R¹ and R² form, in combination with the carbon atoms to which they are bonded, a $C_3$ to $C_{10}$ cycloalkyl ring which may be substituted by the same or different 1 to 3 substituent(s) selected from the group consisting of a halogen atom, a $C_1$ to $C_6$ alkyl group, a $C_1$ to $C_6$ alkoxyl group and a phenoxy group, R³ and R⁴ may be the same or different from each other, and each represents a hydrogen atom;

a $C_1$ to $C_6$ alkyl group which may be substituted by the same or different 1 to 3 substituent(s) selected from the group consisting of a halogen atom, a $C_1$ to $C_6$ alkoxyl group, a $C_1$ to $C_6$ alkylthio group and a phenoxy group;

a halogen atom;

a $C_1$ to $C_6$ alkoxyl group; or a hydroxyl group, or,

R³ and R⁴ form a $C_1$ to $C_6$ alkylidene group or an oxo group in combination thereof; or form, in combination with the carbon atoms to which they are bonded, a $C_3$ to $C_{10}$ cycloalkyl ring which may be substituted by the same or different 1 to 3 substituent(s) selected from the group consisting of a halogen atom, a $C_1$ to $C_6$ alkyl group, a $C_1$ to $C_6$ alkoxyl group and a phenoxy group;

X may be the same or different from each other when n is 2 to 4, and each represents a halogen atom;

a $C_1$ to $C_6$ alkyl group which may be substituted by the same or different 1 to 3 substituent(s) selected from the group consisting of a halogen atom, a $C_1$ to $C_6$ alkoxyl group, a hydroxyl group, a $C_2$ to $C_7$ alkoxycarbonyl group and a phenoxy group;

a $C_2$ to $C_6$ alkenyl group which may be substituted by the same or different 1 to 3 substituent(s) selected from the group consisting of a halogen atom, a $C_1$ to $C_6$ alkoxyl group, a $C_2$ to $C_7$ alkoxycarbonyl group and a phenoxy group;

a $C_2$ to $C_6$ alkynyl group which may be substituted by the same or different 1 to 3 substituent(s) selected from the group consisting of a halogen atom, a $C_1$ to $C_6$ alkoxyl group and a phenoxy group;

an aryl group which may be substituted by the same or different 1 to 6 substituent(s) selected from the group consisting of a halogen atom, a $C_1$ to $C_6$ alkyl group which may be substituted by the same or different 1 to 3 halogen atom(s), a $C_1$ to $C_6$ alkoxyl group, an amino group which may be substituted by the same or different 1 or 2 $C_1$ to $C_6$ alkyl group(s) or acyl group(s), a nitro group, a cyano group, a hydroxyl group, a mercapto group and $C_1$ to $C_6$ alkylthio group;

a heteroaryl group which may be substituted by the same or different 1 to 6 substituent(s) selected from the group consisting of a halogen atom, a $C_1$ to $C_6$ alkyl group which may be substituted by the same or different 1 to 3 halogen atom(s) and a $C_1$ to $C_6$ alkoxyl group;

a $C_1$ to $C_6$ alkoxyl group;

an amino group which may be substituted by the same or different 1 or 2 $C_1$ to $C_6$ alkyl group(s) or acyl group(s);

an acyl group;

a cyano group; or, an N-hydroxy $C_1$ to $C_6$ alkaneimidoyl group the hydrogen atom of the hydroxyl group of which may be substituted by a substituent selected from the group consisting of a $C_1$ to $C_6$ alkyl group, a $C_2$ to $C_6$ alkenyl group, a $C_2$ to $C_6$ alkynyl group, an aralkyl group, an aryl group and a heteroaryl group, Y may be the same or different from each other when m is 2 to 6, and each represents a halogen atom; a $C_1$ to $C_6$ alkyl group; a $C_1$ to $C_6$ alkoxyl group; or a hydroxyl group, n represents an integer of 0 to 4, and m represents an integer of 0 to 6]

or a salt thereof, and (Group b)

(b) one or more fungicides selected from the group consisting of the following mentioned Groups (1) to (28):

Group (1)

a Strobilurin series compound selected from (b-1-1) Azoxystrobin (b-1-2) Kresoxim-methyl (b-1-3) Pyraclostrobin (b-1-4) Picoxystrobin (b-1-5) Fluoxastrobin (b-1-6) Dimoxystrobin (b-1-7) Orysastrobin (b-1-8) Metominostrobin and (b-1-9) Trifloxystrobin, Group (2)

a triazole series compound selected from (b-2-1) Simeconazole (b-2-2) Tebuconazole (b-2-3) Fenbuconazole (b-2-4) Hexaconazole (b-2-5) Imibenconazole (b-2-6) Triadimefon (b-2-7) Tetraconazole (b-2-8) Prothioconazole (b-2-9) Triticonazole (b-2-10) Epoxiconazole (b-2-11) Ipconazole (b-2-12) Metconazole (b-2-13) Propiconazole (b-2-14) Cyproconazole (b-2-15) Difenoconazole (b-2-16) Diniconazole (b-2-17) Fluquinconazole (b-2-18) Flusilazole (b-2-19) Penconazole (b-2-20) Bromuconazole (b-2-21) Triadimenol (b-2-22) Flutriafol (b-2-23) Myclobutanil (b-2-24) Etaconazole and (b-2-25) Bitertanol, Group (3)

an imidazole series compound selected from (b-3-1) Oxpoconazole fumarate (b-3-2) Triflumizole (b-3-3) Imazalil (b-3-4) Imazalil-S (b-3-5) Prochloraz (b-3-6) Pefurazoate and (b-3-7) Triazoxide, Group (4)

a carboxamide series compound selected from (b-4-1) Penthiopyrad (b-4-2) Flutolanil (b-4-3) Furametpyr (b-4-4) Boscalid (b-4-5) Fenhexamid (b-4-6) Cyflufenamid (b-4-7) Tecloftalam (b-4-8) Mandipropamid (b-4-9) Bixafen (b-4-10) Carboxin (b-4-11) Oxycarboxin (b-4-12) Mepronil (b-4-13) Silthiofam
(b-4-14) Thifluzamide
(b-4-15) Flumetover
(b-4-16) Ethaboxam
(b-4-17) Zoxamide
(b-4-18) Tiadinil
(b-4-19) Isotianil
(b-4-20) Diclocymet
(b-4-21) Fenoxanil
(b-4-22) Fluopicolide
(b-4-23) Fluopyram
(b-4-24) Carpropamid
(b-4-25) Tolfenpyrad
(b-4-26) N-[2-(1,3-dimethylbutyl)phenyl]-5-fluoro-1,3-dimethyl-1H-pyrazol-4-carboxamide
(b-4-27) N-{2-[1,1'-bi(cyclopropyl)-2-yl]phenyl}-3-(difluoromethyl)-1-methyl-1H-pyrazol-4-carboxamide
(b-4-28) 3-(Difluoromethyl)-N-(9-isopropyl-1,2,3,4-tetrahydro-1,4-methanonaphthalen-5-yl)-1-methyl-1H-pyrazol-4-carboxamide
(b-4-29) 3-(Difluoromethyl)-N-[4'-(3,3-dimethylbutyn-1-yl)biphenyl-2-yl]-1-methyl-1H-pyrazol-4-carboxamide
(b-4-30) 3-(Difluoromethyl)-N-[4'-(3-methoxy-3-methylbutyn-1-yl)biphenyl-2-yl]-1-methyl-1H-pyrazol-4-carboxamide and
(b-4-31) 3-(Difluoromethyl)-1-methyl-N-[1,2,3,4-tetrahydro-9-(1-methylethyl)-1,4-methanonaphthalen-5-yl]-1H-pyrazol-4-carboxamide,
Group (5)
an acylalanine series compound selected from
(b-5-1) Metalaxyl
(b-5-2) Metalaxyl-M
(b-5-3) Benalaxyl
(b-5-4) Benalaxyl-M (Kiralaxyl) and
(b-5-5) Furalaxyl-M,
Group (6)
a valineamide series compound selected from
(b-6-1) Benthiavalicarb-isopropyl and
(b-6-2) Iprovalicarb;
Group (7)
a sulfoneamide series compound selected from
(b-7-1) Cyazofamid
(b-7-2) Amisulbrom and
(b-7-3) Flusulfamide
Group (8)
a sulfenamide series compound selected from
(b-8-1) Tolylfluanid and
(b-8-2) Dichlofluanid
Group (9)
a carbamate series compound selected from
(b-9-1) Propamocarb
(b-9-2) Propamocarb hydrochloride
(b-9-3) Diethofencarb and
(b-9-4) Pyribencarb
Group (10)
a dithiocarbamate series compound selected from
(b-10-1) Mancozeb
(b-10-2) Maneb
(b-10-3) Propineb
(b-10-4) Zineb
(b-10-5) Metiram
(b-10-6) Ziram
(b-10-7) Thiuram and
(b-10-8) Polycarbamate Group (11)
a dicarboxylimide series compound selected from
(b-11-1) Iprodione
(b-11-2) Procymidone
(b-11-3) Captan
(b-11-4) Vinclozolin
(b-11-5) Chlozolinate and
(b-11-6) Folpet
Group (12)
a guanidine series compound selected from
(b-12-1) Iminoctadine trialbesilate
(b-12-2) Iminoctadine-triacetate
(b-12-3) Guazatine and
(b-12-4) Dodine
Group (13)
a pyrimidine series compound selected from
(b-13-1) Mepanipyrim
(b-13-2) Fenarimol
(b-13-3) Ferimzone
(b-13-4) Cyprodinil
(b-13-5) Pyrimethanil
(b-13-6) Nuarimol
(b-13-7) Dimethirimol
(b-13-8) Bupirimate and
(b-13-9) Diflumetorim
Group (14)
a morpholine series compound selected from
(b-14-1) Dimethomorph
(b-14-2) Fenpropimorph
(b-14-3) Tridemorph
(b-14-4) Dodemorph and
(b-14-5) Flumorph
Group (15)
a benzimidazole series compound selected from
(b-15-1) Thiophanate
(b-15-2) Thiophanatemethyl
(b-15-3) Benomyl
(b-15-4) Carbendazim
(b-15-5) Thiabendazole and
(b-15-6) Fuberidazole
Group (16)
a pyrrole series compound selected from
(b-16-1) Fludioxonil
(b-16-2) Fluoroimide and
(b-16-3) Fenpiclonil
Group (17)
an organophosphorus series compound selected from
(b-17-1) Fosetyl-aluminium
(b-17-2) Edifenphos (EDDP)
(b-17-3) Tolclofos-methyl
(b-17-4) Iprobenfos (IBP) and
(b-17-5) Pyrazophos
Group (18)
a copper series compound selected from
(b-18-1) Cupric hydroxide (Copper hydroxide)
(b-18-2) Copper
(b-18-3) Basic copper chloride (Copper oxychloride)
(b-18-4) Basic copper sulfate (Copper sulfate (tribasic))
(b-18-5) Oxine-copper
(b-18-6) Copper sulfate pentahydrate
(b-18-7) Anhydrous copper sulfate
(b-18-8) Copper nonylphenolsulfonate (Copper nonylphenylsulfate) and
(b-18-9) Copper dodecylbenzene sulfate bis(ethylenediamine) complex salt (DBEDC)

Group (19)
an antibiotics selected from
(b-19-1) Kasugamycin hydrochloride hydrate
(b-19-2) Validamycin
(b-19-3) Polyoxins A to N
(b-19-4) Blastcidin-S benzylamino benzene sulfonate
(b-19-5) Streptomycin
(b-19-6) Natamycin
(b-19-7) Mildiomycin and
(b-19-8) Oxytetracycline
Group (20)
an organic chlorine series compound selected from
(b-20-1) Chlorothalonil (TPN)
(b-20-2) Phthalide and
(b-20-3) Quintozene
Group (21)
a triazolopyrimidine series compound selected from
(b-21-1) 5-Chloro-7-(4-methylpiperidin-1-yl)-6-(2,4,6-trifluorophenyl)[1,2,4]triazolo-[1,5-a]pyrimidine
(b-21-2) 5-Chloro-N-[(1S)-2,2,2-trifluoro-1-methylethyl]-6-(2,4,6-trifluorophenyl)-[1,2,4]triazolo[1,5-a]pyrimidine
(b-21-3) 5-Chloro-N-[(1R)-1,2-dimethylpropyl]-6-(2,4,6-trifluorophenyl)[1,2,4]triazolo[1,5-a]pyrimidine
(b-21-4) 5-(Methoxymethyl)-6-octyl[1,2,4]triazolo[1,5-a]pyrimidin-7-amine and
(b-21-5) 5-Ethyl-6-octyl[1,2,4]triazolo[1,5-a]pyrimidin-7-amine
Group (22)
a benzoyl compound selected from
(b-22-1) Metrafenone and
(b-22-2) 3-(2,3,4-Trimethoxy-6-methylbenzoyl)-5-chloro-2-methoxy-4-methylpyridine
Group (23)
an ethylenediamine series compound selected from
(b-23-1) Isopropyl((1S)-2-methyl-1-{[(4-methylbenzoyl)amino]methyl}propyl)-carbamate
(b-23-2) Isopropyl((1S)-2,2-dimethyl-1-{[(4-methylbenzoyl)amino]methyl}propyl)-carbamate
(b-23-3) Isopropyl((1S)-1-{[(1-benzofuran-2-ylcarbonyl)amino]methyl}-2-methyl-propyl)carbamate
(b-23-4) 2,2,2-Trifluoroethyl((1S)-2-methyl-1-{[(4-methylbenzoyl)amino]methyl}-propyl)carbamate
(b-23-5) 2,2,2-Trifluoroethyl((1S)-2,2-dimethyl-1-{[(4-methylbenzoyl)amino]methyl}-propyl)carbamate
(b-23-6) 2,2,2-Trifluoroethyl((1S)-1-{[(1-benzofuran-2-ylcarbonyl)amino]methyl}-2-methylpropyl)carbamate
(b-23-7) 2,2,2-Trifluoroethyl {(1S)-1-methyl-2-[(4-methylbenzoyl)amino]ethyl}-carbamate
(b-23-8) Benzyl((1S)-2-methyl-1-{[(4-methylbenzoyl)amino]methyl}propyl)carbamate and
(b-23-9) Isopropyl((1R)-2,2,2-trifluoro-1-{[(4-methylbenzoyl)amino]methyl}ethyl)-carbamate
Group (24)
an isoxazolidin series compound selected from
(b-24-1) 3-[5-(4-Chloro phenyl)-2,3-dimethylisoxazolidin-3-yl]pyridine,
(b-24-2) 3-[2,3-Dimethyl-5-(4-methylphenyl)isoxazolidin-3-yl]pyridine and
(b-24-3) 3-[2-Isopropyl-3-methyl-5-(4-chlorophenyl)isoxazolidin-3-yl]pyridine
Group (25)
a quinoline series compound selected from
(b-25-1) Quinoxyfen
(b-25-2) [6-(1,1-Dimethylethyl)-8-fluoro-2,3-dimethylquinoline-4-yl]acetate and
(b-25-3) [6-(1,1-Dimethylethyl)-8-fluoro-2,3-dimethylquinoline-4-yl]methoxyacetate Group (26)
a thiazolidine series compound selected from
(b-26-1) (2Z)-{[2-fluoro-5-(trifluoromethyl)phenyl]thio}[3-(2-methoxyphenyl)-1,3-thiazolidin-2-ylidene]acetonitrile and
(b-26-2) (2Z)-{[2-fluoro-5-(trifluoromethyl)phenyl]thio}[3-(2-methylphenyl)-1,3-thiazolidin-2-ylidene]acetonitrile
Group (27)
a pyrazolinone series compound selected from
(b-27-1) 1-[(2-Propenylthio)carbonyl]-2-(1-methylethyl)-4-(2-methylphenyl)-5-amino-1H-pyrazol-3-one
(b-27-2) 1-[(Ethylthio)carbonyl]-2-(1-methylethyl)-4-(2-methylphenyl)-5-amino-1H-pyrazol-3-one and
(b-27-3) 1-[(Ethylthio)carbonyl]-2-(1-methylethyl)-4-(2,6-dichlorophenyl)-5-amino-1H-pyrazol-3-one, and
Group (28)
other fungicides and mildewcides selected from
(b-28-1) Hydroxyisoxazol (Hymexazol)
(b-28-2) Fluazinam
(b-28-3) Diclomezine
(b-28-4) Tricyclazole
(b-28-5) Cymoxanil
(b-28-6) Famoxadone
(b-28-7) Fenamidone
(b-28-8) Chloropicrin
(b-28-9) Thiadiazine (Milneb)
(b-28-10) Proquinazid
(b-28-11) Spiroxamine
(b-28-12) Fenpropidin
(b-28-13) Dithianon
(b-28-14) Pencycuron
(b-28-15) Isoprothiolane
(b-28-16) Probenazole
(b-28-17) Resveratrol
(b-28-18) Triforine
(b-28-19) Acibenzolar-S-methyl
(b-28-20) Pyroquilon
(b-28-21) Dinocap
(b-28-22) Nickel bis(dimethyldithiocarbamate)
(b-28-23) Etridiazole (Echlomezol)
(b-28-24) Oxadixyl
(b-28-25) Amobam
(b-28-26) Pyrifenox
(b-28-27) Oxolinic acid
(b-28-28) Phosphorous acid
(b-28-29) Dazomet
(b-28-30) Methyl isothiocyanate
(b-28-31) Methasulfocarb
(b-28-32) 1,3-dichloropropene
(b-28-33) Carbam (Metam)
(b-28-34) Methyl iodide (Iodomethane)
(b-28-35) Sulfur
(b-28-36) Lime-sulfur mixed agent (Calcium polysulfide)
(b-28-37) Fentin
(b-28-38) Sodium hypochlorite
(b-28-39) Chinomethionat
(b-28-40) Chloroneb
(b-28-41) Anilazine
(b-28-42) Nitrothal-isopropyl
(b-28-43) Fenitropan
(b-28-44) Dicloran and
(b-28-45) Benthiazole (2-(thiocyanatomethylthio)benzothiazole: TCMTB)
as effective ingredients.
Incidentally, in Compound (I), when m is 0, Ym represents a hydrogen atom, and when n is 0, Xn represents a hydrogen atom.

Effects of the Invention

The plant disease control composition of the present invention shows a broad spectrum against various plant pathogens (for example, rice blast (*Pyricularia oryzae*), gray mold (*Botrytis cinerea*) of tomato, cucumber and kidney bean, etc.) including fungi and bacteria resistant to chemicals, and shows excellent controlling effects (synergistic controlling effects) which could never be expected from a single component alone. Also, it shows high plant disease controlling effects against existing fungi and bacteria resistant to chemicals, and no chemical damage against plants can be admitted.

BEST MODE TO CARRY OUT THE INVENTION

Respective terms used in Compound (I) in the claims and the specification of the present application mean, otherwise specifically mentioned, the definition generally used in the field of chemistry and the definitions described in WO 2005/070917A, JP 2007-1944A, WO 2007/011022A and JP 2007-217353A.

In Compound (I) of the present invention, the $C_1$ to $C_6$ alkyl portion of the "$C_1$ to $C_6$ alkyl group" or "$C_1$ to $C_6$ alkaneimidoyl group" can be a straight or branched alkyl group having 1 to 6 carbon atoms, for example, a methyl group, ethyl group, propyl group, isopropyl group, butyl group, isobutyl group, s-butyl group, t-butyl group, pentyl group, isopentyl group, 2-methylbutyl group, neopentyl group, 1-ethylpropyl group, hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 2-ethylbutyl group, preferably a straight or branched alkyl group having 1 to 5 carbon atoms ($C_1$ to $C_5$ alkyl group), more preferably a straight or branched alkyl group having 1 to 4 carbon atoms ($C_1$ to $C_4$ alkyl group), further more preferably a straight or branched alkyl group having 1 to 3 carbon atoms ($C_1$ to $C_3$ alkyl group), particularly preferably a methyl group, ethyl group or propyl group, most preferably a methyl group or ethyl group.

In Compound (I) of the present invention, the "$C_2$ to $C_6$ alkenyl group" may be either a straight or branched, and can contain 1 or more optional number of double bond(s), and there may be mentioned, for example, a vinyl group, prop-1-en-1-yl group, allyl group, isopropenyl group, but-1-en-1-yl group, but-2-en-1-yl group, but-3-en-1-yl group, 2-methylprop-3-en-1-yl group, 1-methylprop-3-en-1-yl group, pent-1-en-1-yl group, pent-2-en-1-yl group, pent-3-en-1-yl group, pent-4-en-1-yl group, 3-methylbut-2-en-1-yl group, 3-methylbut-3-en-1-yl group, hex-1-en-1-yl group, hex-2-en-1-yl group, hex-3-en-1-yl group, hex-4-en-1-yl group, hex-5-en-1-yl group or 4-methylpent-3-en-1-yl group, preferably a vinyl group, allyl group, iso propenyl group or but-1-en-1-yl group, more preferably an allyl group or isopropenyl group.

In Compound (I) of the present invention, the "$C_2$ to $C_6$ alkynyl group" may be either a straight or branched, and can contain 1 or more optional number of triple bond(s), and there may be mentioned, for example, an ethynyl group, prop-1-yn-1-yl group, prop-2-yn-1-yl group, but-1-yn-1-yl group, but-3-yn-1-yl group, 1-methylprop-2-yn-1-yl group, pent-1-yn-1-yl group, pent-4-yn-1-yl group, hex-1-yn-1-yl group or hex-5-yn-1-yl group, preferably an ethynyl group or prop-1-yn-1-yl group.

In Compound (I) of the present invention, the "aryl group" may be a $C_6$ to $C_{16}$ aromatic hydrocarbon group (6 to 16 carbon atoms), and there may be mentioned, for example, a phenyl group, 1-naphthyl group, 2-naphthyl group, anthracenyl group, phenanthrenyl group, acenaphthylenyl group, etc., preferably a phenyl group, 1-naphthyl group or 2-naphthyl group, more preferably a phenyl group.

In Compound (I) of the present invention, the "heteroaryl group" may be either a monocyclic or polycyclic, and may contain 1 or 2 or more same or different ring-constituting hetero atom(s). A kind of said hetero atom(s) is not particularly limited, and may be mentioned, for example, a nitrogen atom, oxygen atom or sulfur atom. The heteroaryl group may be mentioned, for example, a 5- to 7-membered monocyclic heteroaryl group such as a furyl group, thienyl group, pyrrolyl group, oxazolyl group, isoxazolyl group, dihydro isoxazolyl group, thiazolyl group, isothiazolyl group, imidazolyl group, pyrazolyl group, oxadiazolyl group, thiadiazolyl group, triazolyl group, tetrazolyl group, pyridyl group, azepinyl group, oxazepinyl group, etc., and the polycyclic heteroaryl group constituting the heteroaryl group may be a 8 to 14-membered polycyclic heteroaryl group such as a benzofuranyl group, isobenzofuranyl group, benzothienyl group, indolyl group, isoindolyl group, indazolyl group, benzoxazolyl group, benzisoxazolyl group, benzothiazolyl group, benzisothiazolyl group, benzoxadiazolyl group, benzothiadiazolyl group, benzotriazolyl group, quinolyl group, isoquinolyl group, cinnolinyl group, quinazolinyl group, quinoxalinyl group, phthalazinyl group, naphthyridinyl group, purinyl group, pteridinyl group, carbazolyl group, carbolinyl group, acridinyl group, 2-acridinyl group, 3-acridinyl group, 4-acridinyl group, 9-acridinyl group, phenoxazinyl group, phenothiazinyl group, phenadinyl group, etc., preferably a furyl group, thienyl group, oxazolyl group, pyridyl group, benzofuranyl group or iso benzofuranyl group, more preferably a furyl group, thienyl group, oxazolyl group or pyridyl group, particularly preferably a furyl group or thienyl group.

In Compound (I) of the present invention, the "aralkyl group" is a group in which 1 or 2 or more hydrogen atom(s) (preferably 1 to 3 hydrogen atom(s), more preferably 1 or 2 hydrogen atom(s)) of the above-mentioned "$C_1$ to $C_6$ alkyl group" is/are substituted by the above-mentioned "aryl group", and there may be mentioned, for example, a benzyl group, 1-naphthyl methyl group, 2-naphthyl methyl group, anthracenylmethyl group, phenanthrenylmethyl group, acenaphthylenylmethyl group, diphenylmethyl group, 1-phenethyl group, 2-phenethyl group, 1-(1-naphthyl)ethyl group, 1-(2-naphthyl)ethyl group, 2-(1-naphthyl)ethyl group, 2-(2-naphthyl)ethyl group, 3-phenylpropyl group, 3-(1-naphthyl)propyl group, 3-(2-naphthyl)propyl group, 4-phenylbutyl group, 4-(1-naphthyl)butyl group, 4-(2-naphthyl)butyl group, 5-phenylpentyl group, 5-(1-naphthyl)pentyl group, 5-(2-naphthyl)pentyl group, 6-phenylhexyl group, 6-(1-naphthyl)hexyl group or 6-(2-naphthyl)hexyl group, preferably a benzyl group, diphenylmethyl group, 1-phenethyl group or 2-phenethyl group, more preferably a benzyl group.

In Compound (I) of the present invention, the "$C_3$ to $C_{10}$ cycloalkyl ring" is, for example, a cyclic hydrocarbon group in which an alkylene group having 2 to 9 carbon atoms such as an ethylene group, trimethylene group, tetramethylene group, pentamethylene group, hexamethylene group, heptamethylene group, octamethylene group, etc., is bonded to one carbon atom, preferably a cyclic hydrocarbon group (cyclobutyl ring, cyclopentyl ring or cyclohexyl ring) in which it is formed by bonding a trimethylene group, tetramethylene group or pentamethylene group, more preferably a cyclic hydrocarbon group (cyclohexyl ring) in which it is formed by bonding a pentamethylene group.

In Compound (I) of the present invention, "a halogen atom" is a fluorine atom, chlorine atom, bromine atom or iodine atom, preferably a fluorine atom, chlorine atom or bromine atom, more preferably a fluorine atom or chlorine atom, most preferably a fluorine atom.

In Compound (I) of the present invention, the "$C_1$ to $C_6$ alkoxyl group" is a straight or branched alkoxyl group having 1 to 6 carbon atoms, for example, a methoxy group, ethoxy group, propoxy group, isopropoxy group, butoxy group, isobutoxy group, s-butoxy group, t-butoxy group, pentyloxy group, isopentyloxy group, 2-methylbutoxy group, neopentyloxy group, 1-ethylpropoxy group, hexyloxy group, (4-methylpentyl)-oxy group, (3-methylpentyl)oxy group, (2-methylpentyl)oxy group, (1-methylpentyl)-oxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 2-ethylbutoxy group, preferably a straight or branched alkoxyl group having 1 to 4 carbon atoms ($C_1$ to $C_4$ alkoxyl group), more preferably a methoxy group, ethoxy group or isopropoxy group, further more preferably a methoxy group or ethoxy group, most preferably a methoxy group.

In Compound (I) of the present invention, the "$C_1$ to $C_6$ alkylthio group" is, for example, a straight or branched alkylthio group having 1 to 6 carbon atoms such as a methylthio group, ethylthio group, propylthio group, isopropylthio group, butylthio group, isopentylthio group, neopentylthio group, 3,3-dimethylbutylthio group, 2-ethylbutylthio group, preferably a straight or branched alkylthio group having 1 to 4 carbon atoms, more preferably a methylthio group.

In Compound (I) of the present invention, the "acyl group" may be mentioned, for example, formyl group, a carbonyl group to which the above-mentioned "$C_1$ to $C_6$ alkyl group" is bound ($C_2$ to $C_7$ alkylcarbonyl group), a carbonyl group to which the above-mentioned "$C_2$ to $C_6$ alkenyl group" is bound ($C_3$ to $C_7$ alkenylcarbonyl group), a carbonyl group to which the above-mentioned "aryl group" is bound ("arylcarbonyl group"), a carbonyl group to which the above-mentioned "$C_1$ to $C_6$ alkoxyl group" is bound ($C_2$ to $C_7$ alkoxycarbonyl group) or a carbonyl group to which the above-mentioned "$C_1$ to $C_6$ alkylthio group" is bound ($C_2$ to $C_7$ alkylthio carbonyl group), preferably a formyl group, $C_2$ to $C_5$ alkylcarbonyl group, $C_3$ to $C_5$ alkenyl carbonyl group, benzoyl group, naphthoyl group, $C_2$ to $C_5$ alkoxycarbonyl group or $C_2$ to $C_5$ alkylthio carbonyl group, more preferably a formyl group, $C_2$ to $C_5$ alkylcarbonyl group, benzoyl group or $C_2$ to $C_5$ alkoxycarbonyl group, particularly preferably an acetyl group, methoxycarbonyl group, ethoxycarbonyl group or benzoyl group, most preferably an acetyl group.

In Compound (I) of the present invention, the "$C_2$ to $C_7$ alkoxycarbonyl group" may be mentioned, for example, an alkoxycarbonyl group having 2 to 7 carbon atoms and the alkoxy portion may be straight or branched such as a methoxycarbonyl group, ethoxycarbonyl group, propoxycarbonyl group, etc., preferably an alkoxycarbonyl group having 2 to 4 carbon atoms, more preferably a methoxycarbonyl group.

In Compound (I) of the present invention, the "$C_1$ to $C_6$ alkyl group which may be substituted by the same or different 1 to 3 halogen atom(s)" is, in addition to the above-mentioned "$C_1$ to $C_6$ alkyl group", there may be mentioned, for example, the above-mentioned "$C_1$ to $C_6$ alkyl group" substituted by the same or different 1 to 3 "halogen atom(s)" mentioned above such as a trifluoromethyl group, trichloromethyl group, difluoromethyl group, dichloromethyl group, dibromomethyl group, fluoromethyl group, chloromethyl group, bromomethyl group, iodomethyl group, 2,2,2-trichloroethyl group, 2,2,2-trifluoroethyl group, 2-bromoethyl group, 2-chloroethyl group, 2-fluoroethyl group, 3-chloropropyl group, 3,3,3-trifluoropropyl group, 4-fluorobutyl group, 3-fluoro-2-methylpropyl group, 3,3,3-trifluoro-2-methylpropyl group, 6,6,6-trichlorohexyl group, etc., preferably the above-mentioned "$C_1$ to $C_4$ alkyl group" which may be substituted by the same or different 1 to 3 "halogen atom(s)" mentioned above, more preferably the above-mentioned "$C_1$ to $C_3$ alkyl group" which may be substituted by the same or different 1 to 3 "fluorine atom(s) or chlorine atom(s)", further more preferably a methyl group, ethyl group, propyl group, chloromethyl group or trifluoromethyl group, particularly preferably a methyl group, ethyl group or trifluoromethyl group.

In Compound (I) of the present invention, the "N-hydroxy $C_1$ to $C_6$ alkaneimidoyl group the hydrogen atom of the hydroxyl group of which may be substituted by the substituent(s) selected from the group consisting of a $C_1$ to $C_6$ alkyl group, $C_2$ to $C_6$ alkenyl group, $C_2$ to $C_6$ alkynyl group, aralkyl group, aryl group and heteroaryl group" may be mentioned, for example, an N-hydroxyalkaneimidoyl group having 1 to 6 carbon atoms such as a hydroxyiminomethyl group, N-hydroxyethaneimidoyl group, N-hydroxypropaneimidoyl group and N-hydroxybutaneimidoyl group, and in addition to the above, a group wherein the hydroxyl group of which is substituted by the above-mentioned "$C_1$ to $C_6$ alkyl group", the above-mentioned "$C_2$ to $C_6$ alkenyl group", the above-mentioned "$C_2$ to $C_6$ alkynyl group", the above-mentioned "aralkyl group", the above-mentioned "aryl group" or the above-mentioned "heteroaryl group", which can be, for example, a methoxyiminomethyl group, N-methoxyethaneimidoyl group, N-ethoxyethaneimidoyl group, N-butoxyethaneimidoyl group, N-allyloxyethaneimidoyl group, N-propargyloxyethaneimidoyl group, N-benzyloxyethaneimidoyl group, N-phenoxyethaneimidoyl group, N-pyridyloxyethaneimidoyl group, N-methoxypropaneimidoyl group, N-methoxybutaneimidoyl group or N-methoxyhexaneimidoyl group, preferably an N-hydroxyalkaneimidoyl group having 1 to 4 carbon atoms in which the hydrogen atom(s) of the hydroxyl group(s) of which may be substituted by a substituent(s) selected from the group consisting of a $C_1$ to $C_6$ alkyl group and phenyl group, more preferably a hydroxyiminomethyl group, N-hydroxyethaneimidoyl group, methoxyiminomethyl group, N-methoxyethaneimidoyl group or N-ethoxyethaneimidoyl group, particularly preferably a methoxyiminomethyl group or N-methoxyethaneimidoyl group.

In Compound (I) of the present invention, "the $C_1$ to $C_6$ alkyl group which may be substituted by the same or different 1 to 3 substituent(s) selected from the group consisting of a halogen atom, $C_1$ to $C_6$ alkoxyl group, $C_1$ to $C_6$ alkylthio group and phenoxy group" of $R^1$, etc., may include, in addition to the above-mentioned "$C_1$ to $C_6$ alkyl group which may be substituted by the same or different 1 to 3 halogen atom(s)", for example, the above-mentioned "$C_1$ to $C_6$ alkyl group" substituted by the same or different 1 to 3 "$C_1$ to $C_6$ alkoxyl group(s)" mentioned above such as a methoxymethyl group, ethoxymethyl group, ethoxyethyl group, propoxymethyl group, etc., the above-mentioned "$C_1$ to $C_6$ alkyl group" substituted by the same or different 1 to 3 "$C_1$ to $C_6$ alkylthio group(s)" mentioned above such as a methylthio methyl group, ethylthiomethyl group, ethylthioethyl group, etc., or the above-mentioned "$C_1$ to $C_6$ alkyl group" substituted by the phenoxy group such as a phenoxymethyl group, phenoxyethyl group, etc., and further include the above-mentioned "$C_1$ to $C_6$ alkyl group" substituted by 2 or 3 kinds of the substituents selected from the group consisting of the above-mentioned halogen atom, the above-mentioned $C_1$ to $C_6$ alkoxyl group, the above-mentioned $C_1$ to $C_6$ alkylthio group and phenoxy group, such as a 2-methoxy-1-chloroethyl group, 3-phenoxy-2-bromo-2-methoxypropyl group, 3-phenoxy-2-bromo-2-methylthiopropyl group, etc., preferably a methyl group, ethyl group, propyl group, methoxymethyl group, ethoxymethyl group, phenoxymethyl group or methylthiomethyl group, more preferably a methyl group or ethyl group.

In Compound (I) of the present invention, "the $C_1$ to $C_6$ alkyl group which may be substituted by the same or different 1 to 3 substituent(s) selected from the group consisting of a halogen atom, $C_1$ to $C_6$ alkoxyl group, hydroxyl group, $C_2$ to $C_7$ alkoxycarbonyl group and phenoxy group" of X, etc., may include, in addition to the above-mentioned "$C_1$ to $C_6$ alkyl group which may be substituted by the same or different 1 to 3 halogen atom(s)", for example, the above-mentioned "$C_1$ to $C_6$ alkyl group" substituted by the same or different 1 to 3 "$C_1$ to $C_6$ alkoxyl group(s)" mentioned above such as a methoxymethyl group, ethoxymethyl group, ethoxyethyl group, propoxymethyl group, etc., the above-mentioned "$C_1$ to $C_6$ alkyl group" substituted by 1 to 3 hydroxyl group(s) such as a hydroxymethyl group, 2-hydroxyethyl group, 3-hydroxypropyl group, etc., the above-mentioned "$C_1$ to $C_6$ alkyl group" substituted by the same or different 1 to 3 "$C_2$ to $C_7$ alkoxycarbonyl group(s)" mentioned above such as a methoxycarbonylmethyl group, ethoxycarbonylmethyl group, 2-(methoxycarbonyl)-ethyl group, etc., or the above-mentioned "$C_1$ to $C_6$ alkyl group" substituted by a phenoxy group(s) such as a phenoxymethyl group, phenoxyethyl group, etc., and further include the above-mentioned "$C_1$ to $C_6$ alkyl group" substituted by 2 or 3 kinds of substituents selected from the group consisting of the above-mentioned halogen atom, the above-mentioned $C_1$ to $C_6$ alkoxyl group, hydroxyl group, the above-mentioned $C_2$ to $C_7$ alkoxycarbonyl group and phenoxy group such as a 2-methoxy-1-chloroethyl group, 2-hydroxy-1-chloroethyl group, 3-phenoxy-2-bromo-2-methoxycarbonylpropyl group, etc., preferably a methyl group, ethyl group, propyl group, methoxymethyl group, ethoxymethyl group, phenoxymethyl group, methylthiomethyl group, methoxycarbonylmethyl group or ethoxycarbonylmethyl group, more preferably a methyl group or ethyl group.

In Compound (I) of the present invention, "the $C_2$ to $C_6$ alkenyl group which may be substituted by the same or different 1 to 3 substituent(s) selected from the group consisting of a halogen atom, $C_1$ to $C_6$ alkoxyl group, $C_2$ to $C_7$ alkoxycarbonyl group and phenoxy group" of X, etc., may include, in addition to the above-mentioned "$C_2$ to $C_6$ alkenyl group", for example, the above-mentioned "$C_2$ to $C_6$ alkenyl group" substituted by the same or different 1 to 3 halogen atom(s) such as a 3-chloroallyl group, 4-bromo-2-butenyl group, etc., the above-mentioned "$C_2$ to $C_6$ alkenyl group" substituted by the same or different 1 to 3 "$C_1$ to $C_6$ alkoxyl group(s)" mentioned above such as a 3-methoxy-2-propenyl group, 4-ethoxy-3-butenyl group, etc., the above-mentioned "$C_2$ to $C_6$ alkenyl group" substituted by the same or different 1 to 3 "$C_2$ to $C_7$ alkoxycarbonyl group(s)" mentioned above such as a methoxycarbonylvinyl group, 3-(ethoxycarbonyl)-2-propenyl group, 4-(methoxycarbonyl)-2-butenyl group, etc., or the above-mentioned "$C_2$ to $C_6$ alkenyl group" substituted by a phenoxy group such as a 3-phenoxy-2-butenyl group, etc., and further include the above-mentioned "$C_2$ to $C_6$ alkenyl group" substituted by 2 or 3 kinds of substituents selected from the group consisting of the above-mentioned halogen atom, the above-mentioned $C_1$ to $C_6$ alkoxyl group, the above-mentioned $C_2$ to $C_7$ alkoxycarbonyl group and the phenoxy group such as a 4-methoxy-3-chloro-2-butenyl group, 4-methoxycarbonyl-3-chloro-2-butenyl group, 4-phenoxy-3-chloro-2-butenyl group, etc., preferably a vinyl group, allyl group, isopropenyl group, but-1-en-1-yl group, 3-chloroallyl group, 4-bromo-2-butenyl group, methoxycarbonylvinyl group or 4-methoxycarbonylbutenyl group, more preferably an allyl group or isopropenyl group.

In Compound (I) of the present invention, "the $C_2$ to $C_6$ alkynyl group which may be substituted by the same or different 1 to 3 substituent(s) selected from the group consisting of a halogen atom, $C_1$ to $C_6$ alkoxyl group and phenoxy group" of X, etc., may include, in addition to the above-mentioned "$C_2$ to $C_6$ alkynyl group", for example, the above-mentioned "$C_2$ to $C_6$ alkynyl group" substituted by the same or different 1 to 3 halogen atom(s) such as a 3-chloro-2-propynyl group, 4-bromo-2-butynyl group, etc., the above-mentioned "$C_2$ to $C_6$ alkynyl group" substituted by the same or different 1 to 3 "$C_1$ to $C_6$ alkoxyl group(s)" mentioned above such as a 3-methoxy-2-propynyl group, 4-ethoxy-3-butynyl group, etc., or the above-mentioned "$C_2$ to $C_6$ alkynyl group" substituted by a phenoxy group such as a 3-phenoxy-2-butynyl group, etc., and further include the above-mentioned "$C_2$ to $C_6$ alkynyl group" substituted by 2 or 3 kinds of substituents selected from the group consisting of the above-mentioned halogen atom, the above-mentioned $C_1$ to $C_6$ alkoxyl group and the phenoxy group such as a 4-methoxy-4-chloro-2-butynyl group, 4-phenoxy-4-chloro-2-butynyl group, etc., preferably an ethynyl group, prop-1-yn-1-yl group, 3-chloro-2-propynyl group, 3-methoxy-2-propynyl group, 4-methoxy-4-chloro-2-butynyl group or 4-phenoxy-4-chloro-2-butynyl group, preferably an ethynyl group or prop-1-yn-1-yl group.

In Compound (I) of the present invention, "the amino group which may be substituted by the same or different 1 or 2 $C_1$ to $C_6$ alkyl group(s) or acyl group(s)" of X, etc., may include, in addition to the amino group, the amino group substituted by the same or different 1 or 2 "$C_1$ to $C_6$ alkyl group(s)" mentioned above or by the same or different 1 or 2 "acyl group(s)" mentioned above, preferably the amino group substituted by the same or different 1 or 2 "$C_1$ to $C_4$ alkyl group(s)" mentioned above or the same or different 1 or 2 "acyl group(s)" mentioned above, more preferably a dimethylamino group, diethylamino group or acetylamino group.

In Compound (I) of the present invention, "the $C_1$ to $C_6$ alkylidene group" formed by $R^3$ and $R^4$ in combination, etc., may include, for example, a straight or branched alkylidene group having 1 to 6 carbon atoms such as a methylidene group (methylene group), ethylidene group, propylidene group, isopropylidene group, preferably a straight or branched alkylidene group having 1 to 4 carbon atoms, particularly preferably a methylidene group (methylene group).

In Compound (I) of the present invention, "an aryl group which may be substituted by the same or different 1 to 6 substituent(s) selected from the group consisting of a halogen atom, $C_1$ to $C_6$ alkyl group which may be substituted by the same or different 1 to 3 halogen atom(s), $C_1$ to $C_6$ alkoxyl group, amino group which may be substituted by the same or different 1 or 2 $C_1$ to $C_6$ alkyl group(s) or acyl group(s), nitro group, cyano group, hydroxyl group, mercapto group and $C_1$ to $C_6$ alkylthio group of $R^1$", etc., may include, in addition to the above-mentioned "aryl group", the above-mentioned "aryl group" substituted by the same or different 1 to 6 halogen atom(s) mentioned above, the above-mentioned "aryl group" substituted by the same or different 1 to 6 "$C_1$ to $C_6$ alkyl group(s) which may be substituted by the same or different 1 to 3 halogen atom(s)" mentioned above, the above-mentioned "aryl group" substituted by the same or different 1 to 6 "$C_1$ to $C_6$ alkoxyl group(s)" mentioned above, the above-mentioned "aryl group" substituted by the same or different 1 to 6 "amino group(s) which may be substituted by the same or different 1 or 2 $C_1$ to $C_6$ alkyl group(s) or acyl group(s)" mentioned above, the above-mentioned "aryl group" substituted by 1 to 6 cyano group(s), the above-mentioned "aryl group" substituted by 1 to 6 hydroxyl group(s), the above-mentioned "aryl group" substituted by 1 to 6 mercapto group(s) or the above-mentioned "aryl group" substituted by the same or different 1 to 6 "$C_1$ to $C_6$ alkylthio group(s)" mentioned above, and further includes the above-mentioned "aryl group" substituted by 2 to 6 substituents selected from the above-mentioned halogen atom, the above-mentioned "$C_1$ to $C_6$ alkyl group which may be substituted by the same or different 1 to 3 halogen atom(s)", the above-mentioned "$C_1$ to $C_6$ alkoxyl group", the above-mentioned "amino group which may be substituted by the same or different 1 or 2 $C_1$ to $C_6$ alkyl group(s) or acyl group(s)", nitro group, cyano group, hydroxyl group, mercapto group and the above-mentioned "$C_1$ to $C_6$ alkylthio group", preferably a phenyl group, 1-naphthyl group, 2-naphthyl group, 4-fluorophenyl group, 4-chlorophenyl group, 3-methoxyphenyl group, 3-cyanophenyl group, 2-methylthiophenyl group or 2-trifluoromethylphenyl group, more preferably a phenyl group, 4-fluorophenyl group or 4-chlorophenyl group.

In Compound (I) of the present invention, "a heteroaryl group which may be substituted by the same or different 1 to 6 substituent(s) selected from the group consisting of a halogen atom, $C_1$ to $C_6$ alkyl group which may be substituted by the same or different 1 to 3 halogen atom(s) and $C_1$ to $C_6$ alkoxyl group" of $R^1$, etc., may include, in addition to the above-mentioned "heteroaryl group", for example, the above-mentioned "heteroaryl group" substituted by the same or different 1 to 6 halogen atom(s), the above-mentioned "heteroaryl group" substituted by the same or different 1 to 6 the above-mentioned "$C_1$ to $C_6$ alkyl group(s) which may be substituted by the same or different 1 to 3 halogen atom(s)" or the above-mentioned "heteroaryl group" substituted by the same or different 1 to 6 "$C_1$ to $C_6$ alkoxyl group(s)" mentioned above, further includes the above-mentioned "heteroaryl group" substituted by 2 to 6 kinds of substituents selected from the group consisting of the above-mentioned halogen atom, the above-mentioned "$C_1$ to $C_6$ alkyl group" and the above-mentioned "$C_1$ to $C_6$ alkoxyl group", preferably a furyl group, thienyl group, oxazolyl group, pyridyl group, benzofuranyl group, isobenzofuranyl group, 5-bromofuryl group, 6-chloropyridyl group, 4-trifluoromethylpyridyl group, 3-fluorothienyl group or 3-methoxythienyl group, more preferably a furyl group or thienyl group.

In Compound (I) of the present invention, "the aralkyl group which may be substituted by the same or different 1 to 6 substituent(s) selected from the group consisting of a halogen atom, a $C_1$ to $C_6$ alkyl group which may be substituted by the same or different 1 to 3 halogen atom(s), a $C_1$ to $C_6$ alkoxyl group, an amino group which may be substituted by the same or different 1 or 2 $C_1$ to $C_6$ alkyl group(s) or acyl group(s), a nitro group, a cyano group, a hydroxyl group, a mercapto group and a $C_1$ to $C_6$ alkylthio group" of $R^1$, etc., may include, in addition to the above-mentioned "aralkyl group", the above-mentioned "aralkyl group" substituted by the same or different 1 to 6 halogen atom(s), the above-mentioned "aralkyl group" substituted by the same or different 1 to 6 "$C_1$ to $C_6$ alkyl group(s) which may be substituted by the same or different 1 to 3 halogen atom(s)" mentioned above, the above-mentioned "aralkyl group" substituted by the same or different 1 to 6 "$C_1$ to $C_6$ alkoxyl group(s)" mentioned above, the above-mentioned "aralkyl group" substituted by the same or different 1 to 6 "amino group(s) which may be substituted by the same or different 1 or 2 $C_1$ to $C_6$ alkyl group(s) or acyl group(s)" mentioned above, the above-mentioned "aralkyl group" substituted by 1 to 6 nitro group(s), the above-mentioned "aralkyl group" substituted by 1 to 6 cyano group(s), the above-mentioned "aralkyl group" substituted by 1 to 6 hydroxyl group(s), the above-mentioned "aralkyl group" substituted by 1 to 6 mercapto group(s) or the above-mentioned "aralkyl group" substituted by the same or different 1 to 6 "$C_1$ to $C_6$ alkylthio group(s)" mentioned above, further include the above-mentioned "aralkyl group" substituted by 2 or more substituents selected from the group consisting of the above-mentioned halogen atom, the above-mentioned "$C_1$ to $C_6$ alkyl group which may be substituted by the same or different 1 to 3 halogen atom(s)", the above-mentioned "$C_1$ to $C_6$ alkoxyl group", the above-mentioned "amino group which may be substituted by the same or different 1 or 2 $C_1$ to $C_6$ alkyl group(s) or acyl group(s)", a nitro group, a cyano group, a hydroxyl group, a mercapto group and the above-mentioned "$C_1$ to $C_6$ alkylthio group", and when the aralkyl group has a substituent(s), the said substituent(s) may be bonded to either of or both of the aryl ring or the alkyl group constituting the aralkyl group, preferably a benzyl group, diphenylmethyl group, 1-phenethyl group, 2-phenethyl group, 4-chlorobenzyl group, 3-cyanobenzyl group or 4-methylthio-2-phenethyl group, more preferably a benzyl group.

In Compound (I) of the present invention, "the $C_3$ to $C_{10}$ cycloalkyl ring which may be substituted by the same or different 1 to 3 substituent(s) selected from the group consisting of a halogen atom, a $C_1$ to $C_6$ alkyl group, a $C_1$ to $C_6$ alkoxyl group and a phenoxy group, which is formed in combination with the carbon atoms to which they are bonded" of $R^1$ and $R^2$, etc., may include, in addition to the above-mentioned "$C_3$ to $C_{10}$ cycloalkyl ring", for example, the above-mentioned "$C_3$ to $C_{10}$ cycloalkyl ring" substituted by the same or different 1 to 3 halogen atom(s), the above-mentioned "$C_3$ to $C_{10}$ cycloalkyl ring" substituted by the same or different 1 to 3 "$C_1$ to $C_6$ alkyl group(s)" mentioned above, the above-mentioned "$C_3$ to $C_{10}$ cycloalkyl ring" substituted by the same or different 1 to 3 "$C_1$ to $C_6$ alkoxyl group(s)" mentioned above or the above-mentioned "$C_3$ to $C_{10}$ cycloalkyl ring" substituted by the same or different 1 to 3 phenoxy group(s), further include the above-mentioned "$C_3$ to $C_{10}$ cycloalkyl ring" substituted by 2 to 3 kinds of substituents selected from the group consisting of the above-mentioned halogen atom, the above-mentioned "$C_1$ to $C_6$ alkyl group", the above-mentioned "$C_1$ to $C_6$ alkoxyl group" and phenoxy group, preferably a cyclobutyl ring, cyclopentyl ring, cyclohexyl ring, 2-chlorocyclopentyl ring, 4-methylcyclohexyl ring, 3-methoxycyclohexyl ring or 3-phenoxycyclohexyl ring, more preferably a cyclohexyl ring.

In Compound (I) of the present invention, X can be substituted to an optional substitutable position(s) on the isoquinoline ring with 1 to 4 positions, and when Xs exist 2 to 4 (when n is 2 or more), these may be the same or different from each other.

In Compound (I) of the present invention, Y can be substituted to an optional substitutable position(s) on the quinoline ring with 1 to 6 positions, and when Ys exist 2 to 6 (when m is 2 or more), these may be the same or different from each other.

Compound (I) in the present invention may be made, for example, a mineral acid salt such as a hydrochloride, sulfate, nitrate, etc.: a phosphate; a sulfonate such as a methanesulfonate, ethanesulfonate, benzenesulfonate, p-toluenesulfonate, etc.; or an organic carboxylate such as an acetate, benzoate, oxalate, fumarate, salicylate, etc. (preferably a hydrochloride, sulfate, nitrate, methanesulfonate, oxalate, fumarate or salicylate).

Compound (I) and a salt thereof of the present invention may be made a solvate, and these solvates are also contained in the present invention. Such a solvate is preferably a hydrate.

In Compound (I) of the present invention, there is compound having an asymmetric carbon, and in such a case, the present invention includes a kind of an optical isomer and a mixture of several kinds of optical isomers with an optional ratio.

In Compound (I) of the present invention, $R^1$ and $R^2$ are each (1a) preferably a $C_1$ to $C_6$ alkyl group which may be substituted by the same or different 1 to 3 halogen atom(s) or phenyl group which may be substituted by the same or different 1 to 5 halogen atom(s), (1b) more preferably a methyl group, ethyl group, propyl group, trifluoromethyl group, trifluoroethyl group, phenyl group, fluorophenyl group or chlorophenyl group, $R^3$ and $R^4$ are each (2a) preferably a hydrogen atom, a halogen atom or a $C_1$ to $C_4$ alkyl group, (2b) more preferably a hydrogen atom, fluorine atom, chlorine atom, methyl group or ethyl group, (2c) further more preferably a hydrogen atom, fluorine atom or methyl group, Xn are (3a) preferably X being a halogen atom; $C_1$ to $C_6$ alkyl group; $C_2$ to $C_6$ alkynyl group; aryl group which may be substituted by the same or different 1 to 6 substituent(s) selected from the group consisting of a halogen atom, $C_1$ to $C_6$ alkyl group which may be substituted by the same or different 1 to 3 halogen atom(s) and $C_1$ to $C_6$ alkoxyl group; heteroaryl group which may be substituted by the same or different 1 to 6 substituent(s) selected from the group consisting of a halogen atom, $C_1$ to $C_6$ alkyl group which may be substituted by the same or different 1 to 3 halogen atom(s) and $C_1$ to $C_6$ alkoxyl group; cyano group; or, N-hydroxy-$C_1$ to $C_6$ alkaneimidoyl group the hydrogen atom of the hydroxyl group of which may be substituted by a substituent(s) selected from the group consisting of a $C_1$ to $C_6$ alkyl group and phenyl group, and n is an integer of 0 to 2, (3b) more preferably X being a halogen atom; $C_1$ to $C_4$ alkyl group; $C_2$ to $C_3$ alkynyl group; phenyl group which may be substituted by the same or different 1 or 2 substituents selected from the group consisting of a fluorine atom, chlorine atom, $C_1$ to $C_2$ alkyl group which may be substituted by 1 to 3 fluorine atoms and $C_1$ to $C_2$ alkoxyl group; furyl group, thienyl group, oxazolyl group or pyridyl group each of which may be substituted by the same or different 1 to 3 substituent(s) selected from the group consisting of a fluorine atom, chlorine atom, $C_1$ to $C_2$ alkyl group which may be substituted by 1 to 3 fluorine atoms and $C_1$ to $C_2$ alkoxyl group; cyano group; or, N-hydroxy-$C_1$ to $C_2$ alkaneimidoyl group the hydrogen atom of the hydroxyl group of which may be substituted by a substituent selected from the group consisting of a $C_1$ to $C_2$ alkyl group and phenyl group, and n is an integer of 0 to 2, (3c) further more preferably X being a fluorine atom, chlorine atom, bromine atom, methyl group, ethynyl group, furyl group, thienyl group, cyano group, methoxyethaneimidoyl group, ethoxyethaneimidoyl group or phenoxyethaneimidoyl group, and n is 0 or 1, Ym are (4a) preferably Y being a fluorine atom, chlorine atom, bromine atom or $C_1$ to $C_3$ alkyl group, and m is 0 to 2, (4b) more preferably Y being a fluorine atom, chlorine atom or methyl group, and m is 0 or 1, (4c) further more preferably Y being a fluorine atom or methyl group, and m is 0 or 1.

Also, a compound in which $R^1$ and $R^2$ are selected from (1a) to (1b), $R^3$ and $R^4$ are selected from (2a) to (2c), Xn is selected from (3a) to (3c), Ym is selected from (4a) to (4c), and they are combined is suitable, and there may be mentioned, for example, (A1) a compound wherein $R^1$ and $R^2$ are each a $C_1$ to $C_6$ alkyl group which may be substituted by the same or different 1 to 3 halogen atom(s) or phenyl group which may be substituted by the same or different 1 to 5 halogen atom(s), $R^3$ and $R^4$ are each a hydrogen atom, halogen atom or $C_1$ to $C_4$ alkyl group, X is a halogen atom; $C_1$ to $C_6$ alkyl group; $C_2$ to $C_6$ alkynyl group; aryl group which may be substituted by the same or different 1 to 6 substituent(s) selected from the group consisting of a halogen atom, $C_1$ to $C_6$ alkyl group which may be substituted by the same or different 1 to 3 halogen atom(s) and $C_1$ to $C_6$ alkoxyl group; heteroaryl group which may be substituted by the same or different 1 to 6 substituent(s) selected from the group consisting of a halogen atom, $C_1$ to $C_6$ alkyl group which may be substituted by the same or different 1 to 3 halogen atom(s) and $C_1$ to $C_6$ alkoxyl group; cyano group; or, N-hydroxy-$C_1$ to $C_6$ alkaneimidoyl group the hydrogen atom of the hydroxyl group of which may be substituted by a substituent selected from the group consisting of a $C_1$ to $C_6$ alkyl group and phenyl group, and n is an integer of 0 to 2, Y is a fluorine atom, chlorine atom, bromine atom or $C_1$ to $C_3$ alkyl group, and m is 0 to 2, (A2) a compound wherein $R^1$ and $R^2$ are each a methyl group, ethyl group, propyl group, trifluoromethyl group, trifluoroethyl group, phenyl group, fluorophenyl group or chlorophenyl group, $R^3$ and $R^4$ are each a hydrogen atom, fluorine atom, chlorine atom, methyl group or ethyl group, X is a halogen atom; $C_1$ to $C_4$ alkyl group; $C_2$ to $C_3$ alkynyl group; phenyl group which may be substituted by the same or different 1 or 2 substituents selected from the group consisting of a fluorine atom, chlorine atom, $C_1$ to $C_2$ alkyl group which may be substituted by 1 to 3 fluorine atoms and $C_1$ to $C_2$ alkoxyl group; furyl group, thienyl group, oxazolyl group or pyridyl group each of which may be substituted by the same or different 1 to 3 substituent(s) selected from the group consisting of a fluorine atom, chlorine atom, $C_1$ to $C_2$ alkyl group which may be substituted by 1 to 3 fluorine atoms and $C_1$ to $C_2$ alkoxyl group; cyano group; or, N-hydroxy-$C_1$ to $C_2$ alkaneimidoyl group the hydrogen atom of the hydroxyl group of which may be substituted by a substituent(s) selected from the group consisting of a $C_1$ to $C_2$ alkyl group and phenyl group, and n is an integer of 0 to 2, Y is a fluorine atom, chlorine atom or methyl group, and m is 0 or 1, or (A3) a compound wherein $R^1$ and $R^2$ are each a methyl group, ethyl group, propyl group, trifluoromethyl group, trifluoroethyl group, phenyl group, fluorophenyl group or chlorophenyl group, $R^3$ and $R^4$ are each a hydrogen atom, fluorine atom or methyl group, X is a fluorine atom, chlorine atom, bromine atom, methyl group, ethynyl group, furyl group, thienyl group, cyano group, methoxyethaneimidoyl group, ethoxyethaneimidoyl group or phenoxyethaneimidoyl group, and n is 0 or 1, Y is a fluorine atom or methyl group, and m is 0 or 1.

Further preferred Compound (I) are (a-1) 3-(5-fluoro-3,3-dimethyl-3,4-dihydroisoquinolin-1-yl) quinoline, (a-2) 3-(5-chloro-3,3-dimethyl-3,4-dihydroisoquinolin-1-yl)quinoline,
(a-3) 3-(5-bromo-3,3-dimethyl-3,4-dihydroisoquinolin-1-yl)quinoline,
(a-4) 3-(5-ethynyl-3,3-dimethyl-3,4-dihydroisoquinolin-1-yl)quinoline,
(a-5) 3-(5,6-difluoro-3,3-dimethyl-3,4-dihydroisoquinolin-1-yl)quinoline,
(a-6) 3-(3-ethyl-5-fluoro-3-propyl-3,4-dihydroisoquinolin-1-yl)quinoline,
(a-7) 3-(5-fluoro-3-methyl-3-propyl-3,4-dihydroisoquinolin-1-yl)quinoline,
(a-8) 3-(3-methyl-3-trifluoromethyl-3,4-dihydroisoquinolin-1-yl)quinoline
(a-9) 3-[3-methyl-3-(2,2,2-trifluoroethyl)-3,4-dihydroisoquinolin-1-yl]quinoline,
(a-10) 3-[3-methyl-3-phenyl-3,4-dihydroisoquinolin-1-yl]quinoline,
(a-11) 3-[3-methyl-3-(4-fluorophenyl)-3,4-dihydroisoquinolin-1-yl]quinoline,
(a-12) 3-[3-methyl-3-(4-chlorophenyl)-3,4-dihydroisoquinolin-1-yl]quinoline,
(a-13) 3-(3,3,4,4-tetramethyl-3,4-dihydroisoquinolin-1-yl)quinoline,
(a-14) 3-(5-fluoro-3,3,4,4-tetramethyl-3,4-dihydroisoquinolin-1-yl)quinoline,
(a-15) 3-(5-fluoro-3,3,4,4-tetramethyl-3,4-dihydroisoquinolin-1-yl)-6-fluoroquinoline,
(a-16) 3-(5-fluoro-3,3,4,4-tetramethyl-3,4-dihydroisoquinolin-1-yl)-8-fluoroquinoline,
(a-17) 3-(5-fluoro-3,3,4,4-tetramethyl-3,4-dihydroisoquinolin-1-yl)-8-methylquinoline,
(a-18) 3-(4,4-difluoro-3,3-dimethyl-3,4-dihydroisoquinolin-1-yl)quinoline,
(a-19) 3-(4,5-difluoro-3,3-dimethyl-3,4-dihydroisoquinolin-1-yl)quinoline or
(a-20) 3-(4,4,5-trifluoro-3,3-dimethyl-3,4-dihydroisoquinolin-1-yl)quinoline.

The compounds (I: compound of Group a) in the present invention are known compounds, and can be prepared by the methods, for example, described in WO 2005/070917 pamphlet or in accordance with these methods.

The compound in Group b of the present invention is selected from (B-1) preferably selected from
Group (1)
a Strobilurin series compound selected from
(b-1-1) Azoxystrobin
(b-1-2) Kresoxim-methyl
(b-1-3) Pyraclostrobin
(b-1-4) Picoxystrobin
(b-1-5) Fluoxastrobin
(b-1-6) Dimoxystrobin
(b-1-7) Orysastrobin
(b-1-8) Metominostrobin and
(b-1-9) Trifloxystrobin,
Group (2)
a triazole series compound selected from
(b-2-1) Simeconazole
(b-2-2) Tebuconazole
(b-2-3) Fenbuconazole
(b-2-4) Hexaconazole
(b-2-5) Imibenconazole
(b-2-6) Triadimefon
(b-2-7) Tetraconazole
(b-2-8) Prothioconazole
(b-2-9) Triticonazole
(b-2-10) Epoxiconazole
(b-2-11) Ipconazole
(b-2-12) Metconazole
(b-2-13) Propiconazole
(b-2-14) Cyproconazole
(b-2-15) Difenoconazole
(b-2-16) Diniconazole
(b-2-17) Fluquinconazole
(b-2-18) Flusilazole
(b-2-19) Penconazole
(b-2-20) Bromuconazole
(b-2-21) Triadimenol
(b-2-22) Flutriafol
(b-2-23) Myclobutanil
(b-2-24) Etaconazole and
(b-2-25) Bitertanol,
Group (3)
an imidazole series compound selected from
(b-3-1) Oxpoconazole fumarate
(b-3-2) Triflumizole
(b-3-3) Imazalil
(b-3-4) Imazalil-S
(b-3-5) Prochloraz
(b-3-6) Pefurazoate and
(b-3-7) Triazoxide,
Group (4)
a carboxamide series compound selected from
(b-4-1) Penthiopyrad
(b-4-2) Flutolanil
(b-4-3) Furametpyr
(b-4-4) Boscalid
(b-4-5) Fenhexamid
(b-4-6) Cyflufenamid
(b-4-7) Tecloftalam
(b-4-8) Mandipropamid
(b-4-9) Bixafen
(b-4-10) Carboxin
(b-4-11) Oxycarboxin
(b-4-12) Mepronil
(b-4-13) Silthiofam
(b-4-14) Thifluzamide
(b-4-15) Flumetover
(b-4-16) Ethaboxam
(b-4-17) Zoxamide
(b-4-18) Tiadinil
(b-4-19) Isotianil
(b-4-20) Diclocymet
(b-4-21) Fenoxanil
(b-4-22) Fluopicolide
(b-4-23) Fluopyram
(b-4-24) Carpropamid
(b-4-25) Tolfenpyrad
(b-4-26) N-[2-(1,3-dimethylbutyl)phenyl]-5-fluoro-1,3-dimethyl-1H-pyrazol-4-carboxamide
(b-4-27) N-{2-[1,1'-bi(cyclopropyl)-2-yl]phenyl}-3-(difluoromethyl)-1-methyl-1H-pyrazol-4-carboxamide
(b-4-28) 3-(difluoromethyl)-N-(9-isopropyl-1,2,3,4-tetrahydro-1,4-methanonaphthalen-5-yl)-1-methyl-1H-pyrazol-4-carboxamide
(b-4-29) 3-(difluoromethyl)-N-[4'-(3,3-dimethylbutyn-1-yl)biphenyl-2-yl]-1-methyl-1H-pyrazol-4-carboxamide
(b-4-30) 3-(difluoromethyl)-N-[4'-(3-methoxy-3-methylbutyn-1-yl)biphenyl-2-yl]-1-methyl-1H-pyrazol-4-carboxamide and
(b-4-31) 3-(difluoromethyl)-1-methyl-N-[1,2,3,4-tetrahydro-9-(1-methylethyl)-1,4-methanonaphthalen-5-yl]-1H-pyrazol-4-carboxamide, Group (5)
an acylalanine series compound selected from
(b-5-1) Metalaxyl
(b-5-2) Metalaxyl-M
(b-5-3) Benalaxyl
(b-5-4) Benalaxyl-M and
(b-5-5) Furalaxyl-M,
Group (6)
a valineamide series compound selected from
(b-6-1) Benthiavalicarb-isopropyl and
(b-6-2) Iprovalicarb;
Group (7)
a sulfoneamide series compound selected from
(b-7-1) Cyazofamid
(b-7-2) Amisulbrom and
(b-7-3) Flusulfamide,
Group (8)
a sulfenamide series compound selected from
(b-8-1) Tolylfluanid and
(b-8-2) Dichlofluanid,
Group (9)
a carbamate series compound selected from
(b-9-1) Propamocarb
(b-9-2) Propamocarb hydrochloride
(b-9-3) Diethofencarb and
(b-9-4) Pyribencarb;
Group (10)
a dithiocarbamate series compound selected from
(b-10-1) Mancozeb (Mancozeb)
(b-10-2) Maneb
(b-10-3) Propineb
(b-10-4) Zineb
(b-10-5) Metiram
(b-10-6) Ziram
(b-10-7) Thiuram and
(b-10-8) Polycarbamate;
Group (11)
a dicarboxylimide series compound selected from
(b-11-1) Iprodione
(b-11-2) Procymidone
(b-11-3) Captan
(b-11-4) Vinclozolin
(b-11-5) Chlozolinate and
(b-11-6) Folpet;
Group (12)
a guanidine series compound selected from
(b-12-1) Iminoctadine trialbesilate
(b-12-2) Iminoctadine-triacetate
(b-12-3) Guazatine and
(b-12-4) Dodine;
Group (13)
a pyrimidine series compound selected from
(b-13-1) Mepanipyrim
(b-13-2) Fenarimol
(b-13-3) Ferimzone
(b-13-4) Cyprodinil
(b-13-5) Pyrimethanil
(b-13-6) Nuarimol
(b-13-7) Dimethirimol
(b-13-8) Bupirimate and
(b-13-9) Diflumetorim;
Group (14)
a morpholine series compound selected from
(b-14-1) Dimethomorph
(b-14-2) Fenpropimorph
(b-14-3) Tridemorph
(b-14-4) Dodemorph and
(b-14-5) Flumorph;
Group (15)
a benzimidazole series compound selected from
(b-15-1) Thiophanate
(b-15-2) Thiophanate-methyl
(b-15-3) Benomyl
(b-15-4) Carbendazim
(b-15-5) Thiabendazole and
(b-15-6) Fuberidazole,
Group (16)
a pyrrole series compound selected from
(b-16-1) Fludioxonil
(b-16-2) Fluoroimide and
(b-16-3) Fenpiclonil;
Group (17)
an organophosphorus series compound selected from
(b-17-1) Fosetyl-aluminium
(b-17-2) Edifenphos
(b-17-3) Tolclofos-methyl
(b-17-4) Iprobenfos and
(b-17-5) Pyrazophos,
Group (18)
a copper series compound selected from
(b-18-1) cupric hydroxide
(b-18-2) copper
(b-18-3) basic copper chloride
(b-18-4) basic copper sulfate
(b-18-5) Oxine-copper
(b-18-6) copper sulfate pentahydrate
(b-18-7) anhydrous copper sulfate
(b-18-8) Copper nonylphenolsulfonate and
(b-18-9) dodecyl benzene sulfonic acid bis ethylenediamine copper complex salt,
Group (19)
an antibiotics selected from
(b-19-1) Kasugamycin hydrochloride hydrate
(b-19-2) Validamycin
(b-19-3) Polyoxins A to N
(b-19-4) Blastcidin-S benzylamino benzene sulfonate
(b-19-5) Streptomycin
(b-19-6) Natamycin
(b-19-7) Mildiomycin and
(b-19-8) Oxytetracycline,
Group (20)
an organic chlorine series compound selected from
(b-20-1) Chlorothalonil
(b-20-2) Phthalide and
(b-20-3) Quintozene,
Group (21)
a triazolopyrimidine series compound selected from
(b-21-1) 5-Chloro-7-(4-methylpiperidin-1-yl)-6-(2,4,6-trifluorophenyl)[1,2,4]triazolo-[1,5-a]pyrimidine
(b-21-2) 5-Chloro-N-[(1S)-2,2,2-trifluoro-1-methylethyl]-6-(2,4,6-trifluorophenyl)-[1,2,4]triazolo[1,5-a]pyrimidine
(b-21-3) 5-Chloro-N-[(1R)-1,2-dimethylpropyl]-6-(2,4,6-trifluorophenyl)[1,2,4]triazolo[1,5-a]pyrimidine
(b-21-4) 5-(Methoxymethyl)-6-octyl[1,2,4]triazolo[1,5-a]pyrimidin-7-amine and
(b-21-5) 5-Ethyl-6-octyl[1,2,4]triazolo[1,5-a]pyrimidin-7-amine,
Group (22)
a benzoyl compound selected from
(b-22-1) Metrafenone and
(b-22-2) 3-(2,3,4-Trimethoxy-6-methylbenzoyl)-5-chloro-2-methoxy-4-methylpyridine, Group (23)
an ethylene diamine series compound selected from
(b-23-1) Isopropyl((1S)-2-methyl-1-{[(4-methylbenzoyl)amino]methyl}propyl)-carbamate
(b-23-2) Isopropyl((1S)-2,2-dimethyl-1-{[(4-methylbenzoyl)amino]methyl}propyl)-carbamate
(b-23-3) Isopropyl((1S)-1-{[(1-benzofuran-2-ylcarbonyl)amino]methyl}-2-methyl-propyl)carbamate
(b-23-4) 2,2,2-Trifluoroethyl((1S)-2-methyl-1-{[(4-methylbenzoyl)amino]methyl}-propyl)carbamate
(b-23-5) 2,2,2-Trifluoroethyl((1S)-2,2-dimethyl-1-{[(4-methylbenzoyl)amino]methyl}-propyl)carbamate
(b-23-6) 2,2,2-Trifluoroethyl((1S)-1-{[(1-benzofuran-2-ylcarbonyl)amino]methyl}-2-methylpropyl)carbamate
(b-23-7) 2,2,2-Trifluoroethyl {(1S)-1-methyl-2-[(4-methylbenzoyl)amino]ethyl}-carbamate
(b-23-8) Benzyl((1S)-2-methyl-1-{[(4-methylbenzoyl)amino]methyl}propyl)carbamate and
(b-23-9) Isopropyl((1R)-2,2,2-trifluoro-1-{[(4-methylbenzoyl)amino]methyl}ethyl)-carbamate,
Group (24)
an isoxazolidin series compound selected from
(b-24-1) 3-[5-(4-Chlorophenyl)-2,3-dimethylisoxazolidin-3-yl]pyridine and
(b-24-2) 3-[2,3-Dimethyl-5-(4-methylphenyl)isoxazolidin-3-yl]pyridine and
(b-24-3) 3-[2-Isopropyl-3-methyl-5-(4-chlorophenyl)isoxazolidin-3-yl]pyridine,
Group (25)
a quinoline series compound selected from
(b-25-1) Quinoxyfen
(b-25-2) [6-(1,1-Dimethylethyl)-8-fluoro-2,3-dimethylquinolin-4-yl]acetate and
(b-25-3) [6-(1,1-Dimethylethyl)-8-fluoro-2,3-dimethylquinolin-4-yl]methoxyacetate;
Group (26)
a thiazolidine series compound selected from
(b-26-1) (2Z)-{[2-fluoro-5-(trifluoromethyl)phenyl]thio}[3-(2-methoxyphenyl)-1,3-thiazolidin-2-ylidene]acetonitrile and
(b-26-2) (2Z)-{[2-fluoro-5-(trifluoromethyl)phenyl]thio}[3-(2-methylphenyl)-1,3-thiazolidin-2-ylidene]acetonitrile,
Group (27)
a pyrazolinone series compound selected from
(b-27-1) 1-[(2-Propenylthio)carbonyl]-2-(1-methylethyl)-4-(2-methylphenyl)-5-amino-1H-pyrazol-3-one
(b-27-2) 1-[(Ethylthio)carbonyl]-2-(1-methylethyl)-4-(2-methylphenyl)-5-amino-1H-pyrazol-3-one and
(b-27-3) 1-[(Ethylthio)carbonyl]-2-(1-methylethyl)-4-(2,6-dichlorophenyl)-5-amino-1H-pyrazol-3-one, and
Group (28)
other fungicides and mildewcides selected from
(b-28-1) Hydroxyisoxazol
(b-28-2) Fluazinam
(b-28-3) Diclomezine
(b-28-4) Tricyclazole
(b-28-5) Cymoxanil
(b-28-6) Famoxadone
(b-28-7) Fenamidone
(b-28-8) Chloropicrin
(b-28-9) Thiadiazine
(b-28-10) Proquinazid
(b-28-11) Spiroxamine
(b-28-12) Fenpropidin
(b-28-13) Dithianon
(b-28-14) Pencycuron
(b-28-15) Isoprothiolane
(b-28-16) Probenazole
(b-28-17) Resveratrol
(b-28-18) Triforine
(b-28-19) Acibenzolar-S-methyl
(b-28-20) Pyroquilon
(b-28-21) Dinocap
(b-28-22) Nickel bis(dimethyl dithiocarbamate)
(b-28-23) Etridiazole
(b-28-24) Oxadixyl
(b-28-25) Amobam
(b-28-26) Pyrifenox
(b-28-27) Oxolinic acid and
(b-28-28) Phosphorous acid
(B-2) further preferably selected from
Group (1)
a Strobilurin series compound selected from
(b-1-1) Azoxystrobin
(b-1-2) Kresoxim-methyl
(b-1-3) Pyraclostrobin
(b-1-4) Picoxystrobin
(b-1-5) Fluoxastrobin
(b-1-6) Dimoxystrobin
(b-1-7) Orysastrobin
(b-1-8) Metominostrobin and
(b-1-9) Trifloxystrobin,
Group (2)
a triazole series compound selected from
(b-2-1) Simeconazole
(b-2-2) Tebuconazole
(b-2-3) Fenbuconazole
(b-2-4) Hexaconazole
(b-2-5) Imibenconazole
(b-2-6) Triadimefon
(b-2-7) Tetraconazole
(b-2-8) Prothioconazole
(b-2-9) Triticonazole
(b-2-10) Epoxiconazole
(b-2-11) Ipconazole
(b-2-12) Metconazole
(b-2-13) Propiconazole
(b-2-14) Cyproconazole
(b-2-15) Difenoconazole
(b-2-16) Diniconazole
(b-2-17) Fluquinconazole and
(b-2-18) Flusilazole
Group (3)
an imidazole series compound selected from
(b-3-1) Oxpoconazole fumarate
(b-3-2) Triflumizole
(b-3-3) Imazalil
(b-3-4) Imazalil-S and
(b-3-5) Prochloraz
Group (4)
a carboxamide series compound selected from
(b-4-1) Penthiopyrad
(b-4-2) Flutolanil
(b-4-3) Furametpyr
(b-4-4) Boscalid
(b-4-5) Fenhexamid
(b-4-6) Cyflufenamid
(b-4-7) Tecloftalam
(b-4-8) Mandipropamid
(b-4-9) Bixafen
(b-4-10) Carboxin
(b-4-11) Oxycarboxin
(b-4-12) Mepronil
(b-4-13) Silthiofam (b-4-14) Thifluzamide
(b-4-15) Flumetover
(b-4-16) Ethaboxam
(b-4-17) Zoxamide
(b-4-18) Tiadinil
(b-4-19) Isotianil
(b-4-20) Diclocymet
(b-4-21) Fenoxanil
(b-4-22) Fluopicolide
(b-4-23) Fluopyram
(b-4-24) Carpropamid
(b-4-25) Tolfenpyrad
(b-4-26) N-[2-(1,3-dimethylbutyl)phenyl]-5-fluoro-1,3-dimethyl-1H-pyrazol-4-carboxamide
(b-4-27) N-{2-[1,1'-bi(cyclopropyl)-2-yl]phenyl}-3-(difluoromethyl)-1-methyl-1H-pyrazol-4-carboxamide
(b-4-28) 3-(Difluoromethyl)-N-(9-isopropyl-1,2,3,4-tetrahydro-1,4-methanonaphthalen-5-yl)-1-methyl-1H-pyrazol-4-carboxamide
(b-4-29) 3-(Difluoromethyl)-N-[4'-(3,3-dimethylbutyn-1-yl)biphenyl-2-yl]-1-methyl-1H-pyrazol-4-carboxamide and
(b-4-30) 3-(Difluoromethyl)-N-[4'-(3-methoxy-3-methylbutyn-1-yl)biphenyl-2-yl]-1-methyl-1H-pyrazol-4-carboxamide
Group (5)
an acylalanine series compound selected from
(b-5-1) Metalaxyl
(b-5-2) Metalaxyl-M
(b-5-3) Benalaxyl and
(b-5-4) Benalaxyl-M
Group (6)
a valineamide series compound selected from
(b-6-1) Benthiavalicarb-isopropyl and
(b-6-2) Iprovalicarb;
Group (7)
a sulfoneamide series compound selected from
(b-7-1) Cyazofamid
(b-7-2) Amisulbrom and
(b-7-3) Flusulfamide,
Group (8)
a sulfenamide series compound selected from
(b-8-1) Tolylfluanid and
(b-8-2) Dichlofluanid,
Group (9)
a carbamate series compound selected from
(b-9-1) Propamocarb
(b-9-2) Propamocarb hydrochloride
(b-9-3) Diethofencarb and
(b-9-4) Pyribencarb;
Group (10)
a dithiocarbamate series compound selected from
(b-10-1) Mancozeb
(b-10-2) Maneb
(b-10-3) Propineb
(b-10-4) Zineb
(b-10-5) Metiram
(b-10-6) Ziram
(b-10-7) Thiuram and
(b-10-8) Polycarbamate;
Group (11)
a dicarboxylimide series compound selected from
(b-11-1) Iprodione
(b-11-2) Procymidone
(b-11-3) Captan
(b-11-4) Vinclozolin
(b-11-5) Chlozolinate and
(b-11-6) Folpet;

Group (12)
a guanidine series compound selected from
(b-12-1) Iminoctadine trialbesilate
(b-12-2) Iminoctadine-triacetate
(b-12-3) Guazatine and
(b-12-4) Dodine;
Group (13)
a pyrimidine series compound selected from
(b-13-1) Mepanipyrim
(b-13-2) Fenarimol
(b-13-3) Ferimzone
(b-13-4) Cyprodinil and
(b-13-5) Pyrimethanil;
Group (14)
a morpholine series compound selected from
(b-14-1) Dimethomorph
(b-14-2) Fenpropimorph
(b-14-3) Tridemorph
(b-14-4) Dodemorph and
(b-14-5) Flumorph;
Group (15)
a benzimidazole series compound selected from
(b-15-1) Thiophanate
(b-15-2) Thiophanate-methyl
(b-15-3) Benomyl
(b-15-4) Carbendazim
(b-15-5) Thiabendazole and
(b-15-6) Fuberidazole,
Group (16)
a pyrrole series compound selected from
(b-16-1) Fludioxonil
(b-16-2) Fluoroimide and
(b-16-3) Fenpiclonil;
Group (17)
an organophosphorous series compound selected from
(b-17-1) Fosetyl-aluminium
(b-17-2) Edifenphos and
(b-17-3) Tolclofos-methyl,
Group (18)
a copper series compound selected from
(b-18-1) Cupric hydroxide
(b-18-2) Copper
(b-18-3) Basic copper chloride
(b-18-4) Basic copper sulfate
(b-18-5) Oxine-copper
(b-18-6) Copper sulfate pentahydrate and
(b-18-7) Anhydrous copper sulfate,
Group (19)
an antibiotics selected from
(b-19-1) Kasugamycin hydrochloride hydrate
(b-19-2) Validamycin
(b-19-3) Polyoxins B and D
(b-19-4) Blastcidin-S benzylaminobenzene sulfonate, and
(b-19-5) Streptomycin,
Group (20)
an organic chlorine series compound selected from
(b-20-1) Chlorothalonil
(b-20-2) Phthalide and
(b-20-3) Quintozene,
Group (21)
a triazolopyrimidine series compound selected from
(b-21-1) 5-Chloro-7-(4-methylpiperidin-1-yl)-6-(2,4,6-trifluorophenyl)[1,2,4]triazolo-[1,5-a]pyrimidine
(b-21-2) 5-Chloro-N-[(1S)-2,2,2-trifluoro-1-methylethyl]-6-(2,4,6-trifluorophenyl)-[1,2,4]triazolo[1,5-a]pyrimidine
(b-21-3) 5-Chloro-N-[(1R)-1,2-dimethylpropyl]-6-(2,4,6-trifluorophenyl)[1,2,4]triazolo[1,5-a]pyrimidine (b-21-4) 5-(Methoxymethyl)-6-octyl[1,2,4]triazolo[1,5-a]pyrimidin-7-amine and
(b-21-5) 5-Ethyl-6-octyl[1,2,4]triazolo[1,5-a]pyrimidin-7-amine,
Group (22)
a benzoyl compound selected from
(b-22-1) Metrafenone and
(b-22-2) 3-(2,3,4-Trimethoxy-6-methylbenzoyl)-5-chloro-2-methoxy-4-methylpyridine,
Group (23)
an ethylenediamine series compound selected from
(b-23-1) Isopropyl((1S)-2-methyl-1-{[(4-methylbenzoyl)amino]methyl}propyl)-carbamate
(b-23-2) Isopropyl((1S)-2,2-dimethyl-1-{[(4-methylbenzoyl)amino]methyl}propyl)-carbamate
(b-23-3) Isopropyl((1S)-1-{[(1-benzofuran-2-ylcarbonyl)amino]methyl}-2-methyl-propyl)carbamate
(b-23-4) 2,2,2-Trifluoroethyl((1S)-2-methyl-1-{[(4-methylbenzoyl)amino]methyl}-propyl)carbamate
(b-23-5) 2,2,2-Trifluoroethyl((1S)-2,2-dimethyl-1-{[(4-methylbenzoyl)amino]methyl}-propyl)carbamate
(b-23-6) 2,2,2-Trifluoroethyl((1S)-1-{[(1-benzofuran-2-ylcarbonyl)amino]methyl}-2-methylpropyl)carbamate
(b-23-7) 2,2,2-Trifluoroethyl {(1S)-1-methyl-2-[(4-methylbenzoyl)amino]ethyl}-carbamate
(b-23-8) Benzyl((1S)-2-methyl-1-{[(4-methylbenzoyl)amino]methyl}propyl)carbamate and
(b-23-9) Isopropyl((1R)-2,2,2-trifluoro-1-{[(4-methylbenzoyl)amino]methyl}ethyl)-carbamate,
Group (24)
an isoxazolidine series compound which is
(b-24-1) 3-[5-(4-Chloro phenyl)-2,3-dimethylisoxazolidin-3-yl]pyridine;
Group (25)
a quinoline series compound selected from
(b-25-1) Quinoxyfen and
(b-25-2) [6-(1,1-Dimethylethyl)-8-fluoro-2,3-dimethylquinoline-4-yl]acetate;
Group (26)
a thiazolidine series compound which is
(b-26-1) (2Z)-{[2-fluoro-5-(trifluoromethyl)phenyl]thio}[3-(2-methoxyphenyl)-1,3-thiazolidin-2-ylidene]acetonitrile,
Group (27)
a pyrazolinone series compound which is
(b-27-1) 1-[(2-Propenylthio)carbonyl]-2-(1-methylethyl)-4-(2-methylphenyl)-5-amino-1H-pyrazol-3-one, and
Group (28)
other fungicides and mildewcides selected from
(b-28-1) Hydroxyisoxazol
(b-28-2) Fluazinam
(b-28-3) Diclomezine
(b-28-4) Tricyclazole
(b-28-5) Cymoxanil
(b-28-6) Famoxadone
(b-28-7) Fenamidone
(b-28-8) Chloropicrin
(b-28-9) Thiadiazine
(b-28-10) Proquinazid
(b-28-11) Spiroxamine
(b-28-12) Fenpropidin
(b-28-13) Dithianon
(b-28-14) Pencycuron
(b-28-15) Isoprothiolane
(b-28-16) Probenazole
(b-28-17) Resveratrol
(b-28-18) Triforine
(b-28-19) Acibenzolar-S-methyl
(b-28-20) Pyroquilon
(b-28-21) Dinocap
(b-28-27) Oxolinic acid and
(b-28-28) Phosphorous acid,
(B-3) further more preferably selected from
Group (1)
a Strobilurin series compound selected from
(b-1-1) Azoxystrobin and
(b-1-2) Kresoxim-methyl,
Group (2)
a triazole series compound selected from
(b-2-1) Simeconazole
(b-2-2) Tebuconazole
(b-2-3) Fenbuconazole
(b-2-4) Hexaconazole
(b-2-5) Imibenconazole and
(b-2-6) Triadimefon,
Group (3)
an imidazole series compound selected from
(b-3-1) Oxpoconazole fumarate and
(b-3-2) Triflumizole,
Group (4)
a carboxamide series compound selected from
(b-4-1) Penthiopyrad
(b-4-2) Flutolanil
(b-4-3) Furametpyr
(b-4-4) Boscalid
(b-4-5) Fenhexamid
(b-4-6) Cyflufenamid and
(b-4-7) Tecloftalam,
Group (5)
an acylalanine series compound selected from
(b-5-1) Metalaxyl
(b-5-2) Metalaxyl-M
(b-5-3) Benalaxyl and
(b-5-4) Benalaxyl-M,
Group (6)
a valineamide series compound which is
(b-6-1) Benthiavalicarb-isopropyl,
Group (7)
a sulfoneamide series compound which is
(b-7-1) Cyazofamid,
Group (9)
a carbamate series compound selected from
(b-9-1) Propamocarb hydrochloride and
(b-9-2) Diethofencarb,
Group (10)
a dithiocarbamate series compound selected from
(b-10-1) Mancozeb and
(b-10-2) Maneb,
Group (11)
a dicarboxylimide series compound selected from
(b-11-1) Iprodione
(b-11-2) Procymidone and
(b-11-3) Captan,
Group (12)
a guanidine series compound which is
(b-12-1) Iminoctadine trialbesilate,
Group (13)
a pyrimidine series compound selected from
(b-13-1) Mepanipyrim
(b-13-2) Fenarimol and
(b-13-3) Ferimzone, Group (14)
a morpholine series compound which is
(b-14-1) Dimethomorph,
Group (15)
a benzimidazole series compound which is
(b-15-1) Thiophanate-methyl,
Group (16)
a pyrrole series compound which is
(b-16-1) Fludioxonil,
Group (18)
a copper series compound which is
(b-18-1) cupric hydroxide,
Group (19)
an antibiotics selected from
(b-19-1) Kasugamycin hydrochloride hydrate
(b-19-2) Validamycin, and
(b-19-3) Polyoxins B and D,
Group (20)
an organic chlorine series compound selected from
(b-20-1) Chlorothalonil and
(b-20-2) Phthalide,
Group (23)
an ethylenediamine series compound selected from
(b-23-1) Isopropyl((1S)-2-methyl-1-{[(4-methylbenzoyl)amino]methyl}propyl)carbamate
(b-23-2) Isopropyl((1S)-2,2-dimethyl-1-{[(4-methylbenzoyl)amino]methyl}propyl)-carbamate
(b-23-3) Isopropyl((1S)-1-{[(1-benzofuran-2-ylcarbonyl)amino]methyl}-2-methyl-propyl)carbamate
(b-23-4) 2,2,2-Trifluoroethyl((1S)-2-methyl-1-{[(4-methylbenzoyl)amino]methyl}-propyl)carbamate
(b-23-5) 2,2,2-Trifluoroethyl((1S)-2,2-dimethyl-1-{[(4-methylbenzoyl)amino]methyl}-propyl)carbamate
(b-23-6) 2,2,2-Trifluoroethyl((1S)-1-{[(1-benzofuran-2-ylcarbonyl)amino]methyl}-2-methylpropyl)carbamate
(b-23-7) 2,2,2-Trifluoroethyl {(1S)-1-methyl-2-[(4-methylbenzoyl)amino]ethyl}-carbamate
(b-23-8) Benzyl((1S)-2-methyl-1-{[(4-methylbenzoyl)amino]methyl}propyl)carbamate and
(b-23-9) Isopropyl((1R)-2,2,2-trifluoro-1-{[(4-methylbenzoyl)amino]methyl}ethyl)-carbamate, and
Group (28)
other fungicides and mildewcides selected from
(b-28-2) Fluazinam
(b-28-3) Diclomezine
(b-28-4) Tricyclazole
(b-28-5) Cymoxanil and
(b-28-6) Famoxadone.

The compounds of Group b in the present invention are known compounds, and they can be prepared by, for example, the methods described in The Pesticide Manual (14th Edition) [British Crop Protection Council Pubn., 2006], WO 1997/15552A, WO 2003/070705A, AGROW No. 243 (1995), WO 1999/024413A, WO 2004/016088A, WO 2003/010149A, WO 2003/74491A, WO 2004/35589A, WO 2004/58723A, WO 1999/21851A, WO 2001/10825A, WO 1998/46607A, JP 2000-119275A, WO 2002/38565A, WO 2006/87325A, WO 2005/87773A, WO 2002/02527A, WO 2003/008372A, WO 2005/042474A, WO 2007/111024A, JP 2006-282508A, JP 2000-281678A, WO 2001/92231A, JP 2000-319270A and JP 2000-226374A or in accordance with these methods.

The plant disease control composition of the present invention gives synergistic controlling effects as compared to the case where each effective ingredient is used alone.

The plant disease control composition of the present invention may be used as such, but it is generally used by mixing with a carrier, and depending on necessity, by adding an auxiliary for preparation such as a surfactant, wetting agent, fixing agent, thickener, antiseptics, colorant, stabilizer, etc., to prepare a wettable powder, flowable, water dispersible granule, dust formulation, emulsifiable concentrate, etc., according to the conventionally known method and used suitably. A content of the quinoline compound (I: compound of Group a) as an effective ingredient in these preparations is generally in the range of 0.005 to 99%, preferably in the range of 0.01 to 90%, more preferably in the range of 0.1 to 85% in a weight ratio. Also, a content of the fungicidal compound of Group b as an effective ingredient in these preparations is generally in the range of 0.005 to 99%, preferably in the range of 0.1 to 90% in a weight ratio, and a sum of the quinoline compound (I: compound of Group a) and the fungicidal compound of Group b is generally in the range of 0.005 to 99%, preferably in the range of 0.01 to 90%, more preferably in the range of 0.1 to 85% in a weight ratio. A mixing ratio of the quinoline compound (I: compound of Group a) and the fungicidal compound of Group b is generally 0.01 to 1000 of the fungicidal compound of Group b based on the quinoline compound as 1, preferably 0.1 to 100 of the fungicidal compound of Group b based on the quinoline compound as 1 in a weight ratio.

In the plant disease control composition of the present invention, a total content of the effective ingredients including the quinoline compound (I: compound of Group a) and the fungicidal compound of Group b may vary depending on the form of the preparation, and generally 0.01 to 30% by weight in the dust formulation, 0.1 to 80% by weight in the wettable powder, 0.5 to 20% by weight in the granule, 2 to 50% by weight in the emulsifiable concentrate, 1 to 50% by weight in the flowable preparation, and 1 to 80% by weight in the dry flowable preparation. It is preferably 0.05 to 10% by weight in the dust formulation, 5 to 60% by weight in the wettable powder, 5 to 20% by weight in the emulsifiable concentrate, 5 to 50% by weight in the flowable preparation, and 5 to 50% by weight in the dry flowable preparation. A content of the auxiliary is 0 to 80% by weight, and a content of the carrier is an amount in which total contents of the compounds of the effective ingredients and the auxiliary are deducted from 100% by weight.

The carrier to be used in the above-mentioned composition means a synthetic or natural inorganic or organic substance to be formulated for the purposes of helping the effective ingredients to be reached to the portion to be treated, and making storage, transport and handling of the compounds of effective ingredients easy. Either of the solid or liquid carriers may be used so long as it is generally used for agricultural and horticultural chemicals, and not limited to specific materials. The solid carrier may be mentioned, for example, inorganic substance substances such as bentonite, montmorillonite, kaolinite, diatomaceous earth, white clay, talc, clay, vermiculite, gypsum, calcium carbonate, amorphous silica, ammonium sulfate, etc.; vegetable organic substances such as soybean powder, wood powder, sawdust, wheat powder, lactose, sucrose, glucose, etc.; or urea, etc. The liquid carrier may be mentioned, for example, aromatic hydrocarbons and naphthenes such as toluene, xylene, cumene, etc.; paraffin series hydrocarbons such as n-paraffin, iso-paraffin, liquid paraffin, kerosene, mineral oil, polybutene, etc.; ketones such as acetone, methylethyl ketone, etc.; ethers such as dioxane, diethylene glycol dimethyl ether, etc.; alcohols such as ethanol, propanol, ethylene glycol, etc.; carbonates such as ethylene carbonate, propylene carbonate, butylene carbonate, etc.; aprotic solvents such as dimethylformamide, dimethylsulfoxide, etc.; or water, etc.

Further, to strengthen the effect of the compounds in the composition of the present invention, an auxiliary may be used each singly or in combination depending on the purposes and considering the preparation form of the preparation, treatment methods, etc. As the auxiliary, a surfactant which is generally used for the purpose of emulsifying, dispersing, spreading or/and wetting the agricultural preparation may be mentioned, for example, a nonionic surfactant such as a sorbitane fatty acid ester, polyoxyethylene sorbitane fatty acid ester, sucrose fatty acid ester, polyoxyethylene fatty acid ester, polyoxyethylene resin acid ester, polyoxyethylene fatty acid diester, polyoxyethylene castor oil, polyoxyethylene alkyl ether, polyoxyethylene alkyl phenyl ether, polyoxyethylene dialkyl phenyl ether, formalin condensate of polyoxyethylene alkyl phenyl ether, polyoxyethylene polyoxypropylene block polymer, alkyl polyoxyethylene polyoxypropylene block polymer ether, alkyl phenyl polyoxyethylene polyoxypropylene block polymer ether, polyoxyethylene alkyl amine, polyoxyethylene fatty acidamide, polyoxyethylene bisphenyl ether, polyoxyalkylene benzyl phenyl ether, polyoxyalkylene styrylphenyl ether, polyoxyalkylene adduct of a higher alcohol, and polyoxyethylene ether and ester type silicone and fluorine series surfactant, etc.; an anionic surfactant such as an alkyl sulfate, polyoxyethylene alkyl ether sulfate, polyoxyethylene alkyl phenyl ether sulfate, polyoxyethylene benzyl phenyl ether sulfate, polyoxyethylene styrylphenyl ether sulfate, polyoxyethylene polyoxypropylene block polymersulfate, paraffin sulfonate, alkanesulfonate, AOS, dialkyl sulfosuccinate, alkyl benzene sulfonate, naphthalene sulfonate, dialkyl naphthalene sulfonate, formalin condensate of naphthalene sulfonate, alkyl diphenyl ether disulfonate, lignin sulfonate, polyoxyethylene alkyl phenyl ether sulfonate, polyoxyethylene alkyl ether sulfosuccinic acid half ester, fatty acid salt, N-methyl-fatty acid sarcosinate, resin acid salt, polyoxyethylene alkyl ether phosphate, polyoxyethylene phenyl ether phosphate, polyoxyethylene dialkylphenyl ether phosphate, polyoxyethylene benzylated phenyl ether phosphate, polyoxyethylene benzylated phenyl phenyl ether phosphate, polyoxyethylene styrylated phenyl ether phosphate, polyoxyethylene styrylated phenyl phenyl ether phosphate, polyoxyethylene polyoxypropylene block polymerphosphate, phosphatidylcholine, phosphatidylethanol imine, alkyl phosphate, sodium tripolyphosphate, etc.; a cationic surfactant such as a polyanion type polymer surfactant derived from acrylic acid, acrylonitrile and acrylamido methylpropane sulfonic acid, alkyl trimethyl ammonium chloride, methyl polyoxyethylene alkyl ammonium chloride, alkyl N-methylpyridinium bromide, monomethylated ammonium chloride, dialkyl methylated ammonium chloride, alkyl penta methylpropylene amine dichloride, alkyl dimethyl benzalkonium chloride, benzethonium chloride, etc.; or an amphoteric surfactant such as a dialkyl diaminoethyl betaine, alkyl dimethyl benzyl betaine, etc. A binder to be used as the auxiliary may be mentioned, for example, sodium arginate, polyvinyl alcohol, Gum Arabic, CMC sodium or bentonite, etc., a disintegrator may be mentioned, for example, CMC sodium or croscarmellose sodium sodium, and a stabilizer may be mentioned, for example, a hindered phenol series antioxidant, or a benzotriazole series or hindered amine series UV absorber, etc. A pH adjuster may be mentioned, for example, phosphoric acid, acetic acid or sodium hydroxide, and an antifungal and antiseptic may be mentioned, for example, a fungicide for industrial purpose, an antifungal and antiseptic such as 1,2-benzisothiazolin-3-one, etc. A thickening agent may be mentioned, for example, xanthan gum, guar gum, CMC sodium, Gum Arabic, polyvinyl alcohol or montmorillonite, etc. A defoaming agent may be mentioned, for example, a silicone series compound, and an antifreezing agent may be mentioned, for example, propylene glycol or ethylene glycol, etc. However, these auxiliaries are not limited by the above.

An application method of the composition of the present invention may be mentioned, for example, a foliar spray treatment to individual plants, nursery-box treatment, spray treatment onto the soil surface, soil incorporation after spray treatment onto the soil surface, injection treatment into the soil, soil incorporation after injection treatment into the soil, soil drench, soil incorporation after soil drench, spray treatment to plant seeds, smear treatment to plant seeds, dip treatment to plant seeds or powder dressing treatment to plant seeds, etc., and any application methods generally utilized for a person skilled in the art can give sufficient effects.

Also, a method for controlling plant disease in the present invention includes methods in which a plant disease control composition containing Compound (I) of Group a and the fungicidal compound of Group b as effective ingredients is applied, a plant disease control composition containing Compound (I) of Group a as an effective ingredient and a plant disease control composition containing a fungicidal compound of Group b as an effective ingredient are simultaneously applied, and, either one of the plant disease control composition containing Compound (I) of Group a as an effective ingredient or a plant disease control composition containing a fungicidal compound of Group b as an effective ingredient is firstly applied, and then, the other above-mentioned composition is applied. An hour(s) (term) after applying either one of the plant disease control composition containing Compound (I) of Group a as an effective ingredient or the plant disease control composition containing a fungicidal compound of Group b as an effective ingredient is firstly applied till the other above-mentioned composition is applied is, for example, 1 minute to 2 weeks after applying either one of which is applied, preferably 5 minutes to 1 week after applying either one of which is applied, more preferably 10 minutes to 3 days after applying either one of which is applied.

Further, the plant disease control composition of the present invention can be prepared as a composition containing the quinoline compound (I) and the fungicidal compound of Group b with high concentrations. The high concentration composition can be used as a spreading liquid by diluting with water. The plant disease control composition of the present invention can be also prepared by mixing a composition containing the quinoline compound (I) with a high concentration, and a composition containing the fungicidal compound of Group b with a high concentration at the time of use to prepare a mixture. This high concentration composition can be used as a spreading liquid by diluting with water (tank mix method).

In the plant disease control composition containing the quinoline compound (I) of Group a and the fungicidal compound of Group b as effective ingredients, its applied amount and a concentration to be applied may vary depending on the crops to be applied, diseases to be controlled, degree of occurrence of diseases, preparation form of the compound, application method and various environmental conditions, etc., and when it is sprayed, it is generally 50 to 10,000 g per hectare, preferably 100 to 5,000 g per hectare as an amount of effective ingredients. When the wettable powder, flowable agent or emulsifiable concentrate is used by diluting with water and spreading, its diluting ratio is generally 5 to 50,000-fold, preferably 10 to 20,000-fold, more preferably 15 to 10,000-fold. In case of the seed disinfection, an amount of the fungicide mixture to be used is generally 0.001 to 50 g, preferably 0.01 to 10 g per kg of the seeds. When the composition of the present invention is applied to individual plants by a foliar spray treatment, spray treatment to the soil surface, injection treatment into the soil, or soil drench, the treatment may be carried out after diluting the chemical to be used by a suitable carrier with a suitable concentration. When the composition of the present invention is contacted to plant seeds, the plant seeds may be dipped into the chemical as such. Also, after diluting the chemical to be used in a suitable carrier with a suitable concentration, the plant seeds may be carried out a dip, powder dressing, spray, or smear treatment. An amount of the preparation to be used for powder dressing, spray or smear treatment is generally 0.05 to 50% or so based on the weight of the dry plant seeds, preferably 0.1 to 30%, but the amount to be used is not limited by these ranges, and may vary depending on the form of the preparation or a kind of plant seeds to be treated. Suitable carriers may include, for example, liquid carriers including water and organic solvents such as ethanol, etc.; inorganic substances such as bentonite, montmorillonite, kaolinite, diatomaceous earth, white clay, talc, clay, vermiculite, gypsum, calcium carbonate, amorphous silica, ammonium sulfate, etc., vegetable organic substances such as soybean powder, wood powder, sawdust, wheat powder, lactose, sucrose, glucose, etc.: or solid carriers such as urea, etc., but the present invention is not limited by these.

The individual plants in present specification are those which live with photosynthesis without any movement, more specifically, there may be mentioned, for example, rice, wheat, barley, corn, grape, apple, pear, peach, yellow peach, persimmon, citrus, soybean, kidney bean, strawberry, potato, cabbage, lettuce, tomato, cucumber, eggplant, water melon, sugar beet, spinach, field pea, pumpkin, sugarcane, tobacco, green pepper, sweet potato, taro, konnyaku, sugar beet, cotton, sunflower, tulip, chrysanthemum or turf, etc., but the present invention is not limited by these.

The plant seeds in the present specification are those which store nutrients for embryo plant to germination and to be agriculturally used for breeding, more specifically, there may be mentioned, for example, seeds of corn, soybean, cotton, rice, sugar beet, wheat, barley, sunflower, tomato, cucumber, eggplant, spinach, field pea, pumpkin, sugarcane, tobacco, green pepper and canola, etc.; seed tuber of taro, potato, sweet potato, konnyaku, etc.; bulb of edible Lily bulbs, tulip, etc., or seed bulb of scallion, etc.; or plants artificially generated by operating the gene, etc. Said plants may be mentioned, for example, transformed seeds such as soybean, corn, cotton, etc., to which herbicidal resistance is provided; rice, tobacco, etc., adapted to cold ground; corn, cotton, potato, etc., to which insecticidal substance-producing ability is provided, etc., which are not inherently present in natural world, but the present invention is not limited by these.

The composition of the present invention can be used by mixing with the other agricultural chemicals, soil conditioners or fertilizing substances such as insecticides, acaricides, nematocides, herbicides and plant growth controllers, etc., as a matter of course, and also possible to use as a mixed preparation with these materials. Insecticides may be mentioned, for example, phosphorus series insecticides such as phenitrothione, diazinon, pyridaphenthion, chlorpyrifos, malathion, phenthoate, dimethoate, methyl thiometon, prothiofos, DDVP, acephate, salithion, EPN, etc.; carbamate series insecticides such as NAC, MTMC, BPMC, pirimicarb, carbosulfan, methomyl, etc.; pyrethroid series insecticides such as ethofenprox, silafluofen, permethrin, fenvalerate, etc.; neonicotinoid series insecticides such as dinotefuran, clothianidin, nitenpyram, thiamethoxam, imidacloprid, thiacloprid, acetamiprid, etc.; and fipronil and ethiprole, etc., but the present invention is not limited by these.

The composition and the controlling method of the present invention are effective to, for example, the following mentioned plant diseases. In the following, specific diseases and its fungi or bacteria to be controlled by the present invention may be exemplified:

blast (*Pyricularia oryzae*), sheath blight (*Thanatephorus cucumeris*), brown spot (*Cochliobolus miyabeanus*), "Bakanae" disease (*Gibberella fujikuroi*), seedling blight (*Pythium* spp., *Fusarium* spp., *Trichoderma* spp., *Rhizopus* spp., *Rhizoctonia solanietc*), rice ustilaginoidea virens (*Claviceps virens*) and smut (*Tilletia barelayana*) of rice; powdery mildew (*Erysiphe graminis* f.sp. *hordei*; f.sp. *tritici*), rust (*Puccinia striiformis; Puccinia graminis, Puccinia recondita, Puccinia hordei*), mottle leaf (*Pyrenophora graminea*), net blotch (*Pyrenophora teres*), fusarium blight (*Fusarium graminearum, Fusarium culmorum, Fusarium avenaceum, Microdochium nivale*), snow mould (*Typhula incarnata, Typhula ishikariensis, Micronectriella nivalis*), loose kernel smut (*Ustilago nuda, Ustilago tritici, Ustilago nigra, Ustilago avenae*), stinking smut (*Tilletia caries, Tilletia pancicii*), eye spot (*Pseudocercosporella herpotrichoides*), foot rot (*Rhizoctonia cerealis*), scald (*Rhynchosporium secalis*), leaf blight (*Septoria tritici*), glume blotch (*Leptosphaeria nodorum*), seedling blight (*Fusarium* spp., *Pythium* spp., *Rhizoctonia* spp., *Septoria nodorum, Pyrenophora* spp.), damping off (*Gaeumannomyces graminis*), anthracnose (*Colletotrichum gramaminicola*), ergot (*Claviceps purpurea*) and spot blotch (*Cochliobolus sativus*) of family of wheat; fusarium blight (*Fusarium graminearumetc*), seedling blight (*Fusarium avenaceum, Penicillium* spp, *Pythium* spp., *Rhizoctonia* spp), rust (*Puccinia sorghi*), brown spot (*Cochliobolus heterostrophus*), smut (*Ustilago maydis*), anthracnose (*Colletotrichum gramaminicola*) and Northern leaf spot (*Cochliobolus carbonum*) of corn;

downy mildew (*Plasmopora viticola*), rust (*Phakopsora ampelopsidis*), powdery mildew (*Uncinula necator*), anthracnose (*Elsinoe ampelina*), ripe rot (*Glomerella cingulata*), black rot (*Guignardia bidwellii*), dead arm (*Phomopsis viticola*), fry speck (*Zygophiala jamaicensis*), gray mold (*Botrytis cinerea*), bud blight (*Diaporthe medusaea*), violet root rot (*Helicobasidium mompa*) and white root rot (*Rosellinia necatrix*) of grape vine; powdery mildew (*Podosphaera leucotricha*), scab (*Venturia inaequalis*), alternaria blotch (*Alternaria alternata* (Apple pathotype)), rust (*Gymnosporangium yamadae*), blossom blight (*Monillia mali*), valsa canker (*Valsa ceratosperma*), ring rot (*Botryosphaeria berengeriana*), anthracnose (*Colletotrichum acutatum*), fry speck (*Zygophiala jamaicensis*), sooty blotch (*Gloeodes pomigena*), fruit spot (*Mycosphaerella pomi*), violet root rot (*Helicobasidium mompa*), white root rot (*Rosellinia necatrix*), diaporthe canker (*Phomopsis mali, Diaporthe tanakae*) and blotch (*Diplocarpon mali*) of apple; phoma rot (*Alternaria alternata* (Japanese pear pathotype)), scab (*Venturia nashicola*), rust (*Gymnosporangium haraeanum*), Physalospora canker (*Physalospora piricola*) and canker (*Diaporthe medusaea, Diaporthe eres*) of pear; phytophthora rot (*Phytophthora cactorum*) of European pear; scab (*Cladosporium carpophilum*), phomopsis rot (*Phomopsis* sp.), phytophthora fruit rot (*Phytophthora* sp.) and anthracnose (*Gloeosporium* laeticolor) of peach; anthracnose (*Glomerella cingulata*), young-fruit rot (*Monilinia kusanoi*) and brown rot (*Monilinia fructicola*) of cherry; anthracnose (*Gloeosporium kaki*), angular leaf spot (*Cercospora kaki; Mycosphaerella nawae*), powdery mildew (*Phyllactinia kakikora*) of persimmon; melanose (*Diaporthe citri*), common green mold (*Penicillium digitatum*), blue mold (*Penicillium italicum*) and scab (*Elsinoe fawcettii*) of citrus;

gray mold (*Botrytis cinerea*) of tomato, cucumber, pulse, strawberry, potato, cabbage, eggplant, lettuce, etc.; stem rot (*Sclerotinia sclerotiorum*) of tomato, cucumber, bean, strawberry, potato, rape, cabbage, eggplant, lettuce, etc.; seedling blight (*Rhizoctonia* spp., *Pythium* spp., *Fusarium* spp., *Phythophthora* spp., *Sclerotinia* sclerotiorumetc.) of various kinds of vegetables such as tomato, cucumber, bean, Japanese radish, water melon, eggplant, rape, green pepper, spinach, sugar beet, etc.; downy mildew (*Pseudoperonospora cubensis*), powdery mildew (*Sphaerotheca fuliginea*), anthracnose (*Colletotrichum lagenarium*), gummy stem blight (*Didymella bryoniae*), *fusarium* wilt (*Fusarium oxysporum*) and *plytophthora* rot (*Phytophthora parasitica, Phytophthora melonis, Phytophthora nicotianae, Phytophthora drechsleri, Phytophthora capsicietc*) of oriental melon; early blight (*Alternaria solani*), leaf mold (*Cladosporium fulvam*), late blight (*Phytophthora infestans*), *fusarium* wilt (*Fusarium oxysporum*), root rot (*Pythium myriotylum, Pythium dissotocum*) and anthracnose (*Colletotrichum phomoides*) of tomato; powdery mildew (*Sphaerotheca fuligineaetc*), leaf mold (*Mycovellosiella nattrassii*), late blight (*Phytophthora infestans*) and brown rot (*Phytophthora capsici*) of eggplant; alternaria leaf spot (*Alternaria brassicae*) of rapeseed; alternaria leaf spot (*Alternaria brassicaeetc*), white spot (*Cercosporella brassicae*), blackleg (*Leptospheria maculans*), clubroot (*Plasmodiophora brassicae*) and downy mildew (*Peronospora brassicae*) of Brassica vegetables; foot rot (*Rhizoctonia solani*), yellows (*Fusarium oxysporum*) of cabbage; bottom rot (*Rhizoctonia solani*) and yellows (*Verticillium dahlie*) of Chinese cabbage; rust (*Puccinia allii*), altenaria leaf spot (*Alternaria porri*), southern blight (*Sclerotium rolfsii. Sclerotium rolfsii*) and white tip disease (*Phytophthora porri*) of weish onion; purple stain (*Cercospora kikuchii*), sphaceloma scab (*Elsinoe glycinnes*), black spot (*Diaporthe phaseololum*), rhizoctonia root rot (*Rhizoctonia solani*), stem rot (*Phytophthora megasperma*), downy mildew (*Peronospora manshurica*), rust (*Phakopsora pachyrhizi*) and anthracnose (*Colletotrichum truncatum*) of soybean; anthracnose (*Colletotrichum lindemuthianum*) of kidney bean; leaf spot (*Mycosphaerella personatum*) and brown leaf spot (*Cercospora arachidicola*) of peanuts; powdery mildew (*Erysiphe pisi*) and downy mildew (*Peronospora pisi*) of pea; downy mildew (*Peronospora viciae*) and *phytophthora* rot (*Phytophthora nicotianae*) of broad bean; early blight (*Alternaria solani*), black scurf (*Rhizoctonia solani*), late blight (*Phytophthora infestans*), silver scurf (*Spondylocladium atrovirens*), dry spot (*Fusarium oxysporum, Fusarium solani*) and powdery scab (*Spongospora subterranea*) of potato; cercospora leaf spot (*Cercospora beticola*), downy mildew (*Peronospora schachtii*), aphanomyces root rot (*Aphanomyces cochioides*) and leaf spot (*Phoma batae*) of sugar beet; leaf blight (*Alternaria dauci*) of carrots; powdery mildew (*Sphaerotheca humuli*), phytophthora rot (*Phytophthora nicotianae*), anthracnose (*Gromerella cingulata*) and soft-rotted fruits (*Pythium ultimum* Trow var. *ultimum*) of strawberry;

net blister blight (*Exobasidium reticulatum*), white scab (*Elsinoe leucospila*), anthracnose (*Colletotrichum theae-sinensis*) and gray blight (*Pestalotiopsis longiseta*) of green tea; brown spot (*Alternaria alternata* (Tobacco pathotype)), powdery mildew (*Erysiphe cichoracearum*), anthracnose (*Colletotrichum tabacum*) and black shank (*Phytophthora parasitica*) of tobacco; damping off (*Fusarium oxysporum*) of cotton;

sclerotinia rot (*Sclerotinia sclerotiorum*) of sunflower; black spot (*Diplocarpon rosae*), powdery mildew (*Sphaerotheca pannosa*), phytophthora rot (*Phytophthora megasperma*) and downy mildew (*Peronospora sparsa*) of rose; leaf blight (*Septoria chrysanthemi-indici*), rust (*Puccinia horiana*) and phytophthora rot (*Phytophthora cactorum*) of chrysanthemum; or brown patch (*Rhizoctonia solani*), dollar spot (*Sclerotinia homoeocarpa*), Curvularia leaf blight (*Curvularia geniculata*), rust (*Puccinia zoysiae*), Helminthosporium leaf blight (*Cochliobolus* sp.), scald (*Rhynchosporium secalis*), damping off (*Gaeumannomyces graminis*), anthracnose (*Colletotrichum graminicola*), typhula brown snow blight (*Typhula incarnata*), typhula black snow blight (*Typhula ishikariensis*), sclerotinia snow blight (*Sclerotinia borealis*), fairy rings (*Marasmius oreadesetc*), pythium blight (*Pythium aphanidermatumetc*) and blast (*Pyricularia oryzae*) of turfgrass, but the present invention is not limited by these.

EXAMPLES

In the following, the present invention is more specifically explained by referring to Preparation examples and Test examples. However, the present invention is not limited only by Preparation examples and Test examples. Incidentally, all the numerical value of the formulation amounts of the respective components described in the following Preparation examples mean part(s) by weight.

Compounds A (a-14), B (a-18) and C (a-20) in compound (I: Group a) to be used in the following Preparation examples and Test examples are compounds of compounds Nos. 1-866, 1-929 and 1-930 in WO 2005/070917, respectively, and described in Examples 114, 177 and 178. Their chemical structures are shown in Table 1.

TABLE 1

| Compound | $R^1$ | $R^2$ | $R^3$ | $R^4$ | Xn | Ym |
|---|---|---|---|---|---|---|
| A (a-14) | Me | Me | Me | Me | 5-F | H |
| B (a-18) | Me | Me | F | F | H | H |
| C (a-20) | Me | Me | F | F | 5-F | H |

Also, compounds 2001 to 2009 of the fungicidal compounds in Group b to be used in the following Preparation examples and Test examples are compounds represented by the formula (II):

[Formula 2]

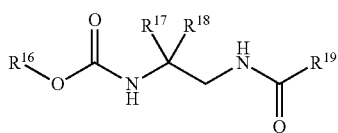

(II)

and $R^{16}$ to $R^{19}$ are each as shown in Table 2.

TABLE 2

| Compound No. | $R^{16}$ | $R^{17}$ | $R^{18}$ | $R^{19}$ |
|---|---|---|---|---|
| 2001 (b-23-1) | iPr | iPr | H | 4-Me-C6H4 |
| 2002 (b-23-2) | iPr | tBu | H | 4-Me-C6H4 |
| 2003 (b-23-3) | iPr | iPr | H | benzofuran-2-yl |
| 2004 (b-23-4) | F3CCH2 | iPr | H | 4-Me-C6H4 |
| 2005 (b-23-5) | F3CCH2 | tBu | H | 4-Me-C6H4 |
| 2006 (b-23-6) | F3CCH2 | iPr | H | benzofuran-2-yl |
| 2007 (b-23-7) | F3CCH2 | Me | H | 4-Me-C6H4 |
| 2008 (b-23-8) | PhCH2CH2 | iPr | H | 4-Me-C6H4 |
| 2009 (b-23-9) | iPr | CF3 | H | 4-Me-C6H4 |

Preparation Example 1

Wettable Powder (a1-1)

Either one of the compounds (10 parts) among Compounds A, B and C as Component I (Group a), either one of the following mentioned compounds (added amount) as Component II (Group b), Neogen Powder (0.5 part), Carplex (0.5 part), GOHSENOL (0.2 part), Radiolite (0.8 part) and H fine powder (used as the remainder so that the total became 100 parts) were crushed and mixed to obtain Wettable powder (a1-1).

Compound (added amount) as Component II (Group b) was Maneb (88 parts), Oxpoconazole fumarate (5 parts), Captan (66 parts), Boscalid (25 parts), Diethofencarb (6 parts), Procymidone (25 parts), Fludioxonil (10 parts), Thiophanate-methyl (35 parts), Fenhexamid (25 parts), Fluazinam (10 parts), Iminoctadine trialbesilate (20 parts), Polyoxins complex (10 parts), Iprodione (25 parts), Penthiopyrad (5 parts), Simeconazole (5 parts), Azoxystrobin (4 parts), Kasugamycin monohydrochloride (1 part), Validamycin (5 parts), Tricyclazole (5 parts), Ferimzone (5 parts), Phthalide (5 parts), Diclomezine (10 parts), Flutolanil (12 parts), Furametpyr (5 parts), Hexaconazole (1 parts), Fenbuconazole (2.2 parts), Tebuconazole (10 parts), Kresoxim-methyl (10 parts), Triadimefon (5 parts), Mepanipyrim (10 parts), Imibenconazole (7.5 parts), Cyflufenamid (0.8 parts), Fenarimol (2 parts), Triflumizole (3 parts), Fosetyl-aluminium (80 parts), Cymoxanil (10 parts), cupric hydroxide (27.6 parts), TPN (20 parts), Propamocarb hydrochloride (80 parts), Cyazofamid (4.7 parts), Metalaxyl (5 parts), Ethaboxam (5 parts), Mancozeb (3.7 parts), Famoxadone (5 parts), Benthiavalicarb-isopropyl (5 parts), Metalaxyl M (5 parts), Dimethomorph (10 parts) or Compound 2001 to 2009 (5 parts).

Preparation Example 2

Wettable Powder (a2-1)

Either one of the compounds (5 parts) among Compounds A, B and C as Component I (Group a), either one of the compounds mentioned in Preparation example 1 as Component II (Group b), Neogen Powder (0.5 part), Carplex (0.5 part), GOHSENOL (0.2 part), Radiolite (0.8 part) and H fine powder (used as the remainder so that the total became 100 parts) were crushed and mixed to obtain Wettable powder (a2-1).

Preparation Example 3

Dust Formulation (b1-1)

Either one of the compounds (2 parts) among Compounds A, B and C as Component I (Group a), either one of the following mentioned compounds (added amount) as Component II (Group b) and clay (used as the remainder so that the total became 100 parts) were uniformly crushed and mixed to obtain Dust formulation (b1-1).

Compounds (added amount) as Component II (Group b) were Captan (40 parts), Boscalid (25 parts), Procymidone (25 parts), Thiophanatemethyl (35 parts), Fluazinam (25 parts), Iminoctadine trialbesilate (15 parts), Polyoxins complex (25 parts), Iprodione (25 parts), Simeconazole (10 parts), Flutolanil (5 parts) or Validamycin (0.3 part).

Preparation Example 4

Dust Formulation (b2-1)

Either one of the compounds (10 parts) among Compounds A, B and C as Component I (Group a), either one of the compounds mentioned in Preparation example 3 as Component II (Group b), flocculant (Driless A: 0.3 part), clay (50 parts) and calcium carbonate (used as the remainder so that the total became 100 parts) were mixed, and pulverized by a pin mill to obtain Dust formulation (b2-1).

Preparation Example 5

Flowable (c1)

Either one of the compounds (5 parts) among Compounds A, B and C as Component I (Group a), either one of the following mentioned compounds (added amount) as Component II, propylene glycol (7 parts), sodium lignosulfate (4 parts), sodium dioctylsulfosuccinate (2 parts) and water (used as the remainder so that the total became 100 parts) were wet pulverized by a sand grinder to obtain Flowable (c1).

Compounds (added amount) as Component II (Group b) were Azoxystrobin (10 parts), Tricyclazole (10 parts), Ferimzone (10 parts), Phthalide (10 parts), Flutolanil (3.5 parts), Hexaconazole (10 parts), Fenbuconazole (11 parts), Tebuconazole (10 parts), Procymidone (20 parts), Cyazofamid (4 parts), TPN (20 parts), Iminoctadine trialbesilate (5 parts) or sulfur (30 parts).

Preparation Example 6

Emulsifiable Concentrate (d1-1)

Either one of the compounds (10 parts) among Compounds A, B and C as Component I (Group a), either one of the following mentioned compounds (added amount) as Component II (Group b), cyclo hexane (10 parts), Tween 20 (surfactant: 20 parts) and xylene (used as the remainder so that the total became 100 parts) were uniformly dissolved and mixed to obtain Emulsifiable concentrate (d1-1).

Compounds (added amount) as Component II (Group b) were Boscalid (20 parts), Procymidone (20 parts), Flutolanil (3.5 parts), Fenbuconazole (11 parts), Tebuconazole (10 parts), Triflumizole (15 parts), TPN (20 parts), Ipconazole (10 parts), Polyoxins complex (5 parts), Tetraconazole (10 parts), Triforine (15 parts), Triadimefon (25 parts) or Difenoconazole (25 parts).

Preparation Example 7

Granules (e1-1)

Either one of the compounds (5 parts) among Compounds A, B and C as Component I (Group a), either one of the following mentioned compounds (added amount) as Component II (Group b), wetting agent (Neopelex No. 6F Powder: 0.5 part), binder (AMICOL No. 1: 3 parts), talc (15 parts) and clay (used as the remainder so that the total became 100 parts) were mixed, hydrolyzed and then, molded by a pellet mill. The obtained molded product was dried and seived to obtain Granules (e1-1).

Compounds (added amount) as Component II (Group b) were Boscalid (25 parts), Procymidone (25 parts), Fludioxonil (10 parts), Fenhexamid (25 parts), Iminoctadine trialbesilate (15 parts), Penthiopyrad (10 parts), Simeconazole (10 parts), Azoxystrobin (10 parts), Validamycin (2.5 parts), Tricyclazole (10 parts), Flutolanil (3.5 parts), Furametpyr (10 parts), Tebuconazole (10 parts), Metalaxyl (5 parts), Mancozeb (7 parts), Diclocymet (3 parts), Metominostrobin (10 parts), Carpropamid (15 parts), Probenazole (10 parts) or Isoprothiolane (5 parts).

Comparative Preparation Example 1

Wettable Powder (a1-2)

Either one of the compounds (10 parts) among Compounds A, B and C as Component I (Group a), Neogen Powder (0.2 part), Carplex (0.2 part), GOHSENOL (0.1 part), Radiolite (1 part) and H fine powder (used as the remainder so that the total became 100 parts) were pulverized and mixed to obtain Wettable powder (a1-2).

Comparative Preparation Example 2

Wettable Powder (a2-2)

Either one of the compounds (5 parts) among Compounds A, B and C as Component I (Group a), Neogen Powder (0.2 part), Carplex (0.2 part), GOHSENOL (0.1 part), Radiolite (1 part) and H fine powder (used as the remainder so that the total became 100 parts) were pulverized and mixed to obtain Wettable powder (a2-2).

Comparative Preparation Example 3

Dust Formulation (b1-2)

Either one of the compounds (2 parts) among Compounds A, B and C as Component I (Group a) and clay (98 parts) were uniformuly pulverized and mixed to obtain Powder (b1-2).

Comparative Preparation Example 4

Dust Formulation (b2-2)

Either one of the compounds (10 parts) among Compounds A, B and C as Component I (Group a), flocculant (Driless A: 0.3 part), clay (50 parts), calcium carbonate (used as the remainder so that the total became 100 parts) were mixed and pulverized by a pin mill to obtain Powder (b2-2).

Comparative Preparation Example 5

Flowable (c1-1)

Either one of the compounds (5 parts) among Compounds A, B and C as Component I (Group a), propylene glycol (7 parts), sodium lignosulfate (4 parts), sodium dioctylsulfosuccinate (2 parts) and water (82 parts) were wet pulverized by a sand grinder to obtain Flowable (c1-1).

Comparative Preparation Example 6

Emulsifiable Concentrate (d1-2)

Either one of the compounds (10 parts) among Compounds A, B and C as Component I (Group a), cyclo hexane (10 parts), xylene (50 parts) and Tween 20 (surfactant: used as the remainder so that the total became 100 parts) were uniformly dissolved and mixed to obtain Emulsifiable concentrate (d1-2).

Comparative Preparation Example 7

Granules (e1-2)

Either one of the compounds (5 parts) among Compounds A, B and C as Component I (Group a), wetting agent (Neopelex No. 6F Powder: 0.5 part), binder (AMICOL No. 1: 3 parts), talc (15 parts) and clay (used as the remainder so that the total became 100 parts) were uniformly mixed, hydrolyzed, and then, molded by a pellet mill. The obtained molded product was dried and seived to obtain Granules (e1-2).

Test Example 1

Tomato Gray Mold Preventive Test
(Diethofencarb-Resistant Strain)

In a greenhouse, tomato (variety: Ohgata-Fukuju) planted in a plastic pot having a diameter of 5 cm was grown to the 2nd to 3rd-leaf stage. Wettable powder prepared according to Preparation example 1 and Preparation example 2 were diluted to a predetermined concentration with water, and sprayed with a spray gun with 10 ml per 2 pots. After drying the chemical liquid, a conidiospore suspension prepared from *Botrytis cinerea* (Diethofencarb-resistant strain) which had been previously cultured on a MY medium were inoculated by spraying. After inoculation, the pots were placed in a high-humidity chamber (20 to 22° C.), and after 2 days, the pots were taken out and controlling effects were examined. In the examination, a ratio of lesion area occupied per whole leaflet of tomato was determined according to the indexes of the following mentioned degree of diseases. Also, from the average degree of diseases of each treated district, the control value was calculated from the following numerical formula. Incidentally, as a comparison, Wettable powder prepared according to Comparative preparation example 1 and Comparative preparation example 2 were similarly tested, and controlling effects were examined. The results of the spreading test and the theoretical value according to the Colby's formula are shown in Table 3.

Index of Degree of Disease
Index Degree of Disease
  0 No lesion
  1 Lesion area is less than 1/3 of whole leaflet
  2 Lesion area is 1/3 or more and less than 2/3 of whole leaflet
  3 Lesion area is 2/3 or more of whole leaflet Incidentally, average values of the each treated district and non-treated district were used as the degree of diseases.

The control value was calculated from the following formula.

Control value=(1−Ratio of diseased leaflets in the treated district/Ratio of diseased leaflets in the non-treated district)×100

Here, Colby's formula is X=P+Q−P×Q/100, wherein X is a theoretical value of the control value, P is a control value where a certain chemical is spread alone, and Q is a control value where chemicals to be used in combination are spread in admixture.

TABLE 3

| Effective ingredient in the preparation | Treatment concentration (ppm) | Control value | Theoretical value |
|---|---|---|---|
| A + Maneb | 10 + 177.5 | 90 | 86 |
| A + Oxpoconazole fumarate | 10 + 10 | 100 | 83 |
| A + Captan | 10 + 133.3 | 100 | 89 |
| A + Boscalid | 10 + 50 | 100 | 86 |
| A + Diethofencarb | 10 + 12.5 | 90 | 83 |
| A + Procymidone | 10 + 50 | 100 | 86 |
| A + Fludioxonil | 10 + 20 | 100 | 94 |
| A + Thiophanate-methyl | 10 + 70 | 100 | 91 |
| A + Fenhexamid | 10 + 50 | 100 | 92 |

TABLE 3-continued

| Effective ingredient in the preparation | Treatment concentration (ppm) | Control value | Theoretical value |
|---|---|---|---|
| A + Fluazinam | 10 + 20 | 100 | 83 |
| A + Iminoctadine trialbesilate | 10 + 40 | 100 | 94 |
| A + Polyoxins complex | 10 + 20 | 100 | 93 |
| A + Iprodione | 10 + 50 | 100 | 94 |
| A + Penthiopyrad | 10 + 10 | 100 | 89 |
| A + Simeconazole | 10 + 10 | 100 | 89 |
| B + Maneb | 10 + 177.5 | 100 | 86 |
| B + Oxpoconazole fumarate | 10 + 10 | 100 | 83 |
| B + Captan | 10 + 133.3 | 100 | 89 |
| B + Boscalid | 10 + 50 | 100 | 86 |
| B + Diethofencarb | 10 + 12.5 | 100 | 83 |
| B + Procymidone | 10 + 50 | 100 | 86 |
| B + Fludioxonil | 10 + 20 | 100 | 94 |
| B + Thiophanate-methyl | 10 + 70 | 100 | 91 |
| B + Fenhexamid | 10 + 50 | 100 | 92 |
| B + Fluazinam | 10 + 20 | 95 | 83 |
| B + Iminoctadine trialbesilate | 10 + 40 | 100 | 94 |
| B + Polyoxins complex | 10 + 20 | 100 | 93 |
| B + Iprodione | 10 + 50 | 100 | 94 |
| B + Penthiopyrad | 10 + 10 | 100 | 89 |
| B + Simeconazole | 10 + 10 | 100 | 89 |
| C + Maneb | 10 + 177.5 | 95 | 83 |
| C + Oxpoconazole fumarate | 10 + 10 | 95 | 80 |
| C + Captan | 10 + 133.3 | 100 | 87 |
| C + Boscalid | 10 + 50 | 100 | 83 |
| C + Diethofencarb | 10 + 12.5 | 93 | 80 |
| C + Procymidone | 10 + 50 | 93 | 83 |
| C + Fludioxonil | 10 + 20 | 100 | 93 |
| C + Thiophanate-methyl | 10 + 70 | 100 | 89 |
| C + Fenhexamid | 10 + 50 | 100 | 90 |
| C + Fluazinam | 10 + 20 | 90 | 80 |
| C + Iminoctadine trialbesilate | 10 + 40 | 100 | 93 |
| C + Polyoxins complex | 10 + 20 | 100 | 92 |
| C + Iprodione | 10 + 50 | 100 | 93 |
| C + Penthiopyrad | 10 + 10 | 100 | 87 |
| C + Simeconazole | 10 + 10 | 98 | 87 |
| Maneb | 177.5 | 17 | |
| Oxpoconazole fumarate | 10 | 0 | |
| Captan | 133.3 | 33 | |
| Boscalid | 50 | 17 | |
| Diethofencarb | 12.5 | 0 | |
| Procymidone | 50 | 17 | |
| Fludioxonil | 20 | 67 | |
| Thiophanate-methyl | 70 | 43 | |
| Fenhexamid | 50 | 50 | |
| Fluazinam | 20 | 0 | |
| Iminoctadine trialbesilate | 40 | 67 | |
| Polyoxins complex | 20 | 60 | |
| Iprodione | 50 | 67 | |
| Penthiopyrad | 10 | 33 | |
| Simeconazole | 10 | 33 | |
| A | 10 | 83 | |
| B | 10 | 83 | |
| C | 10 | 80 | |

From the results shown in the above-mentioned Table 3, it could be understood that synergistic effects could be obtained when Compound A, B or C and the compound of Group b are used in combination. Incidentally, even when Compound A, B or C and the compound of Group b are used in combination, no chemical damage symptom was admitted in the plant material, tomato (variety: Ohgata-Fukuju).

Test Example 2

Rice Blast Preventive Test

In a greenhouse, rice (variety: Sachikaze) planted in a plastic pot having a diameter of 5 cm was grown to the 3rd to 4th-leaf stage. Spray was carried out in the same manner as in Test example 1, and after 3 days from the spray, a conidiospore suspension prepared from *Pyricularia oryzae* which had been previously cultured on an oatmeal medium were inoculated by spraying. After inoculation, the pots were placed in a high-humidity chamber (20 to 23° C.), and taken out on the next day and transferred into a greenhouse. Controlling effects were examined after 7 days from the inoculation. In the examination, a ratio of lesion area occupied per one leaf of rice was determined according to the same index as in Test example 1, and the control value and the theoretical value according to Colby's formula were similarly calculated. The results are shown in Table 4.

TABLE 4

| Effective ingredient in the preparation | Treatment concentration (ppm) | Control value | Theoretical value |
|---|---|---|---|
| A + Azoxystrobin | 10 + 8 | 67 | 38 |
| A + Kasugamycin monohydrochloride | 10 + 2 | 50 | 38 |
| A + Validamycin | 10 + 10 | 50 | 44 |
| A + Tricyclazole | 10 + 10 | 50 | 36 |
| A + Ferimzone | 10 + 10 | 60 | 38 |
| A + Phthalide | 10 + 10 | 60 | 51 |
| A + Diclomezine | 10 + 20 | 50 | 44 |
| A + Flutolanil | 10 + 25 | 50 | 38 |
| A + Furametpyr | 10 + 10 | 60 | 36 |
| A + Compound 2001 | 10 + 5 | 67 | 55 |
| A + Compound 2002 | 10 + 5 | 78 | 55 |
| A + Compound 2003 | 10 + 5 | 78 | 66 |
| A + Compound 2004 | 10 + 5 | 97 | 78 |
| A + Compound 2005 | 10 + 5 | 98 | 78 |
| A + Compound 2006 | 10 + 5 | 97 | 78 |
| A + Compound 2007 | 10 + 5 | 100 | 78 |
| A + Compound 2008 | 10 + 5 | 78 | 55 |
| A + Compound 2009 | 10 + 5 | 100 | 78 |
| B + Azoxystrobin | 10 + 8 | 90 | 84 |
| B + Kasugamycin monohydrochloride | 10 + 2 | 90 | 84 |
| B + Validamycin | 10 + 10 | 98 | 86 |
| B + Tricyclazole | 10 + 10 | 98 | 84 |
| B + Ferimzone | 10 + 10 | 97 | 84 |
| B + Phthalide | 10 + 10 | 97 | 88 |
| B + Diclomezine | 10 + 20 | 98 | 86 |
| B + Flutolanil | 10 + 25 | 98 | 84 |
| B + Furametpyr | 10 + 10 | 97 | 84 |
| B + Compound 2001 | 10 + 5 | 96 | 89 |
| B + Compound 2002 | 10 + 5 | 96 | 89 |
| B + Compound 2003 | 10 + 5 | 98 | 91 |
| B + Compound 2004 | 10 + 5 | 100 | 94 |
| B + Compound 2005 | 10 + 5 | 100 | 94 |
| B + Compound 2006 | 10 + 5 | 100 | 94 |
| B + Compound 2007 | 10 + 5 | 100 | 94 |
| B + Compound 2008 | 10 + 5 | 100 | 89 |
| B + Compound 2009 | 10 + 5 | 100 | 94 |
| C + Azoxystrobin | 10 + 8 | 95 | 79 |
| C + Kasugamycin monohydrochloride | 10 + 2 | 89 | 79 |
| C + Validamycin | 10 + 10 | 98 | 82 |
| C + Tricyclazole | 10 + 10 | 95 | 79 |
| C + Ferimzone | 10 + 10 | 97 | 79 |
| C + Phthalide | 10 + 10 | 97 | 84 |
| C + Diclomezine | 10 + 20 | 100 | 82 |
| C + Flutolanil | 10 + 25 | 95 | 79 |
| C + Furametpyr | 10 + 10 | 97 | 79 |
| C + Compound 2001 | 10 + 5 | 95 | 85 |
| C + Compound 2002 | 10 + 5 | 96 | 85 |
| C + Compound 2003 | 10 + 5 | 98 | 89 |
| C + Compound 2004 | 10 + 5 | 100 | 93 |
| C + Compound 2005 | 10 + 5 | 100 | 93 |
| C + Compound 2006 | 10 + 5 | 100 | 93 |
| C + Compound 2007 | 10 + 5 | 100 | 93 |
| C + Compound 2008 | 10 + 5 | 100 | 85 |
| C + Compound 2009 | 10 + 5 | 100 | 93 |
| Azoxystrobin | 8 | 6.7 | |
| Kasugamycin monohydrochloride | 2 | 6.7 | |
| Validamycin | 10 | 17 | |
| Tricyclazole | 10 | 3.3 | |
| Ferimzone | 10 | 6.7 | |
| Phthalide | 10 | 27 | |
| Diclomezine | 20 | 17 | |
| Flutolanil | 25 | 6.7 | |
| Furametpyr | 10 | 3.3 | |
| Compound 2001 | 5 | 33 | |
| Compound 2002 | 5 | 33 | |
| Compound 2003 | 5 | 50 | |
| Compound 2004 | 5 | 67 | |
| Compound 2005 | 5 | 67 | |
| Compound 2006 | 5 | 67 | |
| Compound 2007 | 5 | 67 | |
| Compound 2008 | 5 | 33 | |
| Compound 2009 | 5 | 67 | |
| A | 10 | 33 | |
| B | 10 | 83 | |
| C | 10 | 78 | |

From the results shown in the above-mentioned Table 4, it could be understood that synergistic effects could be obtained when Compound A, B or C and the compound of Group b are used in combination. Incidentally, even when Compound A, B or C and the compound of Group b are used in combination, no chemical damage symptom was admitted in the plant material, rice (variety: Sachikaze).

Test Example 3

Rice Blast Curative Test

In a greenhouse, rice (variety: Sachikaze) planted in a plastic pot having a diameter of 5 cm was grown to the 3rd to 4th-leaf stage. A conidiospore suspension prepared from *Pyricularia oryzae* which had been previously cultured on an oatmeal medium were inoculated by spraying. After inoculation, the pots were placed in a high-humidity chamber (20 to 23° C.) and taken out on the next day, and spray was carried out in the same manner as in Test example 1. After drying the chemical liquid, the pots were transferred into a greenhouse, and controlling effects were examined after 7 days from the spray. In the examination, a ratio of lesion area occupied per one leaf of rice was determined according to the same index as in Test example 1, and the control value and the theoretical value according to Colby's formula were similarly calculated. The results are shown in Table 5.

TABLE 5

| Effective ingredient in the preparation | Treatment concentration (ppm) | Control value | Theoretical value |
|---|---|---|---|
| A + Azoxystrobin | 10 + 8 | 96 | 79 |
| A + Kasugamycin monohydrochloride | 10 + 2 | 96 | 77 |
| A + Validamycin | 10 + 10 | 89 | 77 |
| A + Tricyclazole | 10 + 10 | 89 | 77 |
| A + Ferimzone | 10 + 10 | 89 | 77 |
| A + Phthalide | 10 + 10 | 89 | 77 |
| A + Diclomezine | 10 + 20 | 89 | 77 |
| A + Flutolanil | 10 + 25 | 89 | 77 |
| A + Furametpyr | 10 + 10 | 89 | 77 |
| B + Azoxystrobin | 10 + 8 | 96 | 86 |
| B + Kasugamycin monohydrochloride | 10 + 2 | 96 | 85 |
| B + Validamycin | 10 + 10 | 94 | 85 |
| B + Tricyclazole | 10 + 10 | 94 | 85 |
| B + Ferimzone | 10 + 10 | 94 | 85 |

TABLE 5-continued

| Effective ingredient in the preparation | Treatment concentration (ppm) | Control value | Theoretical value |
|---|---|---|---|
| B + Phthalide | 10 + 10 | 96 | 85 |
| B + Diclomezine | 10 + 20 | 96 | 85 |
| B + Flutolanil | 10 + 25 | 94 | 85 |
| B + Furametpyr | 10 + 10 | 100 | 87 |
| C + Azoxystrobin | 10 + 8 | 94 | 86 |
| C + Kasugamycin monohydrochloride | 10 + 2 | 96 | 85 |
| C + Validamycin | 10 + 10 | 96 | 85 |
| C + Tricyclazole | 10 + 10 | 96 | 85 |
| C + Ferimzone | 10 + 10 | 96 | 85 |
| C + Phthalide | 10 + 10 | 96 | 85 |
| C + Diclomezine | 10 + 20 | 91 | 85 |
| C + Flutolanil | 10 + 25 | 91 | 85 |
| C + Furametpyr | 10 + 10 | 94 | 87 |
| Azoxystrobin | 8 | 1.8 | |
| Kasugamycin monohydrochloride | 2 | 0 | |
| Validamycin | 10 | 0 | |
| Tricyclazole | 10 | 0 | |
| Ferimzone | 10 | 0 | |
| Phthalide | 10 | 0 | |
| Diclomezine | 20 | 0 | |
| Flutolanil | 25 | 0 | |
| Furametpyr | 10 | 11 | |
| A | 10 | 79 | |
| B | 10 | 86 | |
| C | 10 | 86 | |

From the results shown in the above-mentioned Table 5, it could be understood that synergistic effects could be obtained when Compound A, B or C and the compound of Group b are used in combination. Incidentally, even when Compound A, B or C and the compound of Group b are used in combination, no chemical damage symptom was admitted in the plant material, rice (variety: Sachikaze).

Test Example 4

Cucumber Powdery Mildew Preventive Test

In a greenhouse, cucumber (variety: Sagamihanpaku) planted in a plastic pot having a diameter of 5 cm was grown to the 3rd to 5th-leaf stage. Spray was carried out in the same manner as in Test example 1, and 3 days after the spray, a conidiospore suspension prepared from *Sphaerotheca fuliginea* were inoculated on the leaf surface. After inoculation, the pots were placed in a thermostatic greenhouse (20 to 25° C.), and controlling effects were examined after 7 days from the inoculation. In the examination, a ratio of lesion area occupied per one leaf of cucumber was determined according to the same index as in Test example 1, and the control value and the theoretical value according to Colby's formula were similarly calculated. The results are shown in Table 6.

TABLE 6

| Effective ingredient in the preparation | Treatment concentration (ppm) | Control value | Theoretical value |
|---|---|---|---|
| A + Hexaconazole | 10 + 2 | 67 | 58 |
| A + Fenbuconazole | 10 + 4.4 | 75 | 63 |
| A + Tebuconazole | 10 + 20 | 75 | 67 |
| A + Simeconazole | 10 + 10 | 67 | 50 |
| A + Kresoxim-methyl | 10 + 20 | 67 | 58 |
| A + Triadimefon | 10 + 10 | 67 | 50 |
| A + Mepanipyrim | 10 + 20 | 60 | 50 |
| A + Imibenconazole | 10 + 15 | 73 | 67 |
| A + Cyflufenamid | 10 + 1.7 | 83 | 67 |
| A + Fenarimol | 10 + 4 | 93 | 83 |
| A + Triflumizole | 10 + 6 | 83 | 67 |
| B + Hexaconazole | 10 + 2 | 93 | 67 |
| B + Fenbuconazole | 10 + 4.4 | 83 | 71 |
| B + Tebuconazole | 10 + 20 | 100 | 73 |
| B + Simeconazole | 10 + 10 | 83 | 60 |
| B + Kresoxim-methyl | 10 + 20 | 92 | 67 |
| B + Triadimefon | 10 + 10 | 73 | 60 |
| B + Mepanipyrim | 10 + 20 | 67 | 60 |
| B + Imibenconazole | 10 + 15 | 83 | 73 |
| B + Cyflufenamid | 10 + 1.7 | 93 | 73 |
| B + Fenarimol | 10 + 4 | 92 | 87 |
| B + Triflumizole | 10 + 6 | 93 | 73 |
| C + Hexaconazole | 10 + 2 | 85 | 71 |
| C + Fenbuconazole | 10 + 4.4 | 88 | 74 |
| C + Tebuconazole | 10 + 20 | 100 | 77 |
| C + Simeconazole | 10 + 10 | 88 | 65 |
| C + Kresoxim-methyl | 10 + 20 | 90 | 71 |
| C + Triadimefon | 10 + 10 | 76 | 65 |
| C + Mepanipyrim | 10 + 20 | 72 | 65 |
| C + Imibenconazole | 10 + 15 | 90 | 77 |
| C + Cyflufenamid | 10 + 1.7 | 100 | 77 |
| C + Fenarimol | 10 + 4 | 98 | 88 |
| C + Triflumizole | 10 + 6 | 98 | 77 |
| Hexaconazole | 2 | 17 | |
| Fenbuconazole | 4.4 | 27 | |
| Tebuconazole | 20 | 33 | |
| Simeconazole | 10 | 0 | |
| Kresoxim-methyl | 20 | 17 | |
| Triadimefon | 10 | 0 | |
| Mepanipyrim | 20 | 0 | |
| Imibenconazole | 15 | 33 | |
| Cyflufenamid | 1.7 | 33 | |
| Fenarimol | 4 | 67 | |
| Triflumizole | 6 | 33 | |
| A | 10 | 50 | |
| B | 10 | 60 | |
| C | 10 | 65 | |

From the results shown in the above-mentioned Table 6, it could be understood that synergistic effects could be obtained when Compound A, B or C and the compound of Group b are used in combination. Incidentally, even when Compound A, B or C and the compound of Group b are used in combination, no chemical damage symptom was admitted in the plant material, cucumber (variety: Sagamihanpaku).

Test Example 5

Cucumber Powdery Mildew Curative Test

In a greenhouse, cucumber (variety: Sagamihanpaku) planted in a plastic pot having a diameter of 5 cm was grown to the 3rd to 5th-leaf stage. A conidiospore suspension prepared from *Sphaerotheca fuliginea* were inoculated on the leaf surface, and the pots were transferred into a thermostatic greenhouse (20 to 25° C.). Two days after inoculation, spray was carried out in the same manner as in Test example 1. After drying the chemical liquid, the pots were transferred into a thermostatic greenhouse, and controlling effects were examined after 7 days from the inoculation. In the examination, a ratio of lesion area occupied per one leaf of cucumber was determined according to the same index as in Test example 1, and the control value and the theoretical value according to Colby's formula were similarly calculated. The results are shown in Table 7.

TABLE 7

| Effective ingredient in the preparation | Treatment concentration (ppm) | Control value | Theoretical value |
|---|---|---|---|
| A + Hexaconazole | 10 + 2 | 100 | 92 |
| A + Fenbuconazole | 10 + 4.4 | 100 | 92 |
| A + Tebuconazole | 10 + 20 | 100 | 89 |
| A + Simeconazole | 10 + 10 | 89 | 78 |
| A + Kresoxim-methyl | 10 + 20 | 96 | 89 |
| A + Triadimefon | 10 + 10 | 96 | 89 |
| A + Mepanipyrim | 10 + 20 | 100 | 92 |
| A + Imibenconazole | 10 + 15 | 100 | 92 |
| A + Cyflufenamid | 10 + 1.7 | 100 | 89 |
| A + Fenarimol | 10 + 4 | 100 | 93 |
| A + Triflumizole | 10 + 6 | 100 | 89 |
| B + Hexaconazole | 10 + 2 | 100 | 93 |
| B + Fenbuconazole | 10 + 4.4 | 100 | 93 |
| B + Tebuconazole | 10 + 20 | 100 | 91 |
| B + Simeconazole | 10 + 10 | 100 | 82 |
| B + Kresoxim-methyl | 10 + 20 | 98 | 91 |
| B + Triadimefon | 10 + 10 | 100 | 91 |
| B + Mepanipyrim | 10 + 20 | 100 | 93 |
| B + Imibenconazole | 10 + 15 | 100 | 93 |
| B + Cyflufenamid | 10 + 1.7 | 100 | 91 |
| B + Fenarimol | 10 + 4 | 100 | 94 |
| B + Triflumizole | 10 + 6 | 100 | 91 |
| C + Hexaconazole | 10 + 2 | 100 | 93 |
| C + Fenbuconazole | 10 + 4.4 | 100 | 93 |
| C + Tebuconazole | 10 + 20 | 100 | 91 |
| C + Simeconazole | 10 + 10 | 100 | 82 |
| C + Kresoxim-methyl | 10 + 20 | 97 | 91 |
| C + Triadimefon | 10 + 10 | 100 | 91 |
| C + Mepanipyrim | 10 + 20 | 100 | 93 |
| C + Imibenconazole | 10 + 15 | 100 | 93 |
| C + Cyflufenamid | 10 + 1.7 | 100 | 91 |
| C + Fenarimol | 10 + 4 | 100 | 94 |
| C + Triflumizole | 10 + 6 | 97 | 91 |
| Hexaconazole | 2 | 75 | |
| Fenbuconazole | 4.4 | 75 | |
| Tebuconazole | 20 | 67 | |
| Simeconazole | 10 | 33 | |
| Kresoxim-methyl | 20 | 67 | |
| Triadimefon | 10 | 67 | |
| Mepanipyrim | 20 | 75 | |
| Imibenconazole | 15 | 75 | |
| Cyflufenamid | 1.7 | 67 | |
| Fenarimol | 4 | 78 | |
| Triflumizole | 6 | 67 | |
| A | 10 | 67 | |
| B | 10 | 73 | |
| C | 10 | 73 | |

From the results shown in the above-mentioned Table 7, it could be understood that synergistic effects could be obtained when Compound A, B or C and the compound of Group b are used in combination. Incidentally, even when Compound A, B or C and the compound of Group b are used in combination, no chemical damage symptom was admitted in the plant material, cucumber (variety: Sagamihanpaku).

Test Example 6

Tomato Late Blight Preventive Test

In a greenhouse, tomato (variety: Ohgata-Fukuju) planted in a plastic pot having a diameter of 5 cm was grown to the 2nd to 3rd-leaf stage. Spray was carried out in the same manner as in Test example 1, and after drying the chemical liquid, the pots were transferred into a greenhouse. After 3 days from the spray, a sporangium suspension of *Phytophthora infestans* were inoculated by spraying. After inoculation, the pots were placed in a high-humidity chamber (20 to 22° C.), transferred into a greenhouse on the next day, and controlling effects were examined after 7 days from the inoculation. A ratio of lesion area occupied per one leaf of tomato was determined according to the same index as in Test example 1, and the control value and the theoretical value according to Colby's formula were similarly calculated. The results are shown in Table 8.

TABLE 8

| Effective ingredient in the preparation | Treatment concentration (ppm) | Control value | Theoretical value |
|---|---|---|---|
| A + Fosetyl-aluminium | 10 + 160 | 17 | 8.3 |
| A + Cymoxanil | 10 + 20 | 75 | 50 |
| A + cupric hydroxide | 10 + 55.3 | 33 | 17 |
| A + TPN | 10 + 40 | 17 | 0 |
| A + Propamocarb hydrochloride | 10 + 160 | 17 | 0 |
| A + Cyazofamid | 10 + 9.4 | 100 | 92 |
| A + Metalaxyl | 10 + 10 | 67 | 58 |
| A + Ethaboxam | 10 + 10 | 93 | 83 |
| A + Mancozeb | 10 + 7.5 | 83 | 67 |
| A + Famoxadone | 10 + 10 | 33 | 17 |
| A + Azoxystrobin | 10 + 8 | 83 | 67 |
| A + Benthiavalicarb-isopropyl | 10 + 10 | 93 | 80 |
| A + Metalaxyl M | 10 + 10 | 42 | 33 |
| A + Dimethomorph | 10 + 20 | 75 | 50 |
| B + Fosetyl-aluminium | 10 + 160 | 33 | 8.3 |
| B + Cymoxanil | 10 + 20 | 100 | 50 |
| B + cupric hydroxide | 10 + 55.3 | 33 | 17 |
| B + TPN | 10 + 40 | 40 | 0 |
| B + Propamocarb hydrochloride | 10 + 160 | 33 | 0 |
| B + Cyazofamid | 10 + 9.4 | 100 | 92 |
| B + Metalaxyl | 10 + 10 | 83 | 58 |
| B + Ethaboxam | 10 + 10 | 97 | 83 |
| B + Mancozeb | 10 + 7.5 | 83 | 67 |
| B + Famoxadone | 10 + 10 | 33 | 17 |
| B + Azoxystrobin | 10 + 8 | 83 | 67 |
| B + Benthiavalicarb-isopropyl | 10 + 10 | 100 | 80 |
| B + Metalaxyl M | 10 + 10 | 67 | 33 |
| B + Dimethomorph | 10 + 20 | 83 | 50 |
| C + Fosetyl-aluminium | 10 + 160 | 17 | 8.3 |
| C + Cymoxanil | 10 + 20 | 92 | 50 |
| C + cupric hydroxide | 10 + 55.3 | 33 | 17 |
| C + TPN | 10 + 40 | 33 | 0 |
| C + Propamocarb hydrochloride | 10 + 160 | 17 | 0 |
| C + Cyazofamid | 10 + 9.4 | 100 | 92 |
| C + Metalaxyl | 10 + 10 | 75 | 58 |
| C + Ethaboxam | 10 + 10 | 92 | 83 |
| C + Mancozeb | 10 + 7.5 | 83 | 67 |
| C + Famoxadone | 10 + 10 | 33 | 17 |
| C + Azoxystrobin | 10 + 8 | 83 | 67 |
| C + Benthiavalicarb-isopropyl | 10 + 10 | 92 | 80 |
| C + Metalaxyl M | 10 + 10 | 67 | 33 |
| C + Dimethomorph | 10 + 20 | 70 | 50 |
| Fosetyl-aluminium | 160 | 8.3 | |
| Cymoxanil | 20 | 50 | |
| cupric hydroxide | 55.3 | 17 | |
| TPN | 40 | 0 | |
| Propamocarb hydrochloride | 160 | 0 | |
| Cyazofamid | 9.4 | 92 | |
| Metalaxyl | 10 | 58 | |
| Ethaboxam | 10 | 83 | |
| Mancozeb | 7.5 | 67 | |
| Famoxadone | 10 | 17 | |
| Azoxystrobin | 8 | 67 | |
| Benthiavalicarb-isopropyl | 10 | 80 | |
| Metalaxyl M | 10 | 33 | |
| Dimethomorph | 20 | 50 | |
| A | 10 | 0 | |
| B | 10 | 0 | |
| C | 10 | 0 | |

From the results shown in the above-mentioned Table 8, it could be understood that synergistic effects could be obtained when Compound A, B or C and the compound of Group b are used in combination. Incidentally, even when Compound A, B or C and the compound of Group b are used in combination, no chemical damage symptom was admitted in the plant material, tomato (variety: Ohgata-Fukuju).

Test Example 7

Tomato Late Blight Curative Test

In a greenhouse, tomato (variety: Ohgata-Fukuju) planted in a plastic pot having a diameter of 5 cm was grown to the 2nd to 3rd-leaf stage. A sporangium suspension of *Phytophthora infestans* were inoculated, the pots were placed in a high-humidity chamber (20 to 22° C.), and taken out on the next day and spray was carried out in the same manner as in Test example 1. After drying the chemical liquid, the pots were transferred into a greenhouse, and controlling effects were examined after 7 days from the inoculation. A ratio of lesion area occupied per one leaf of tomato was determined according to the same index as in Test example 1, and the control value and the theoretical value according to Colby's formula were similarly calculated. The results are shown in Table 9.

TABLE 9

| Effective ingredient in the preparation | Treatment concentration (ppm) | Control value | Theoretical value |
|---|---|---|---|
| A + Fosetyl-aluminium | 10 + 160 | 33 | 25 |
| A + Cymoxanil | 10 + 20 | 83 | 67 |
| A + cupric hydroxide | 10 + 55.3 | 17 | 0 |
| A + TPN | 10 + 40 | 6.7 | 0 |
| A + Propamocarb hydrochloride | 10 + 160 | 33 | 0 |
| A + Cyazofamid | 10 + 9.4 | 33 | 0 |
| A + Metalaxyl | 10 + 10 | 76 | 67 |
| A + Ethaboxam | 10 + 10 | 76 | 67 |
| A + Mancozeb | 10 + 7.5 | 6.7 | 0 |
| A + Famoxadone | 10 + 10 | 17 | 0 |
| A + Azoxystrobin | 10 + 8 | 6.7 | 0 |
| A + Benthiavalicarb-isopropyl | 10 + 10 | 70 | 67 |
| A + Metalaxyl M | 10 + 10 | 20 | 17 |
| A + Dimethomorph | 10 + 20 | 13 | 0 |
| B + Fosetyl-aluminium | 10 + 160 | 37 | 25 |
| B + Cymoxanil | 10 + 20 | 92 | 67 |
| B + cupric hydroxide | 10 + 55.3 | 33 | 0 |
| B + TPN | 10 + 40 | 33 | 0 |
| B + Propamocarb hydrochloride | 10 + 160 | 33 | 0 |
| B + Cyazofamid | 10 + 9.4 | 33 | 0 |
| B + Metalaxyl | 10 + 10 | 83 | 67 |
| B + Ethaboxam | 10 + 10 | 83 | 67 |
| B + Mancozeb | 10 + 7.5 | 17 | 0 |
| B + Famoxadone | 10 + 10 | 17 | 0 |
| B + Azoxystrobin | 10 + 8 | 17 | 0 |
| B + Benthiavalicarb-isopropyl | 10 + 10 | 83 | 67 |
| B + Metalaxyl M | 10 + 10 | 33 | 17 |
| B + Dimethomorph | 10 + 20 | 33 | 0 |
| C + Fosetyl-aluminium | 10 + 160 | 33 | 25 |
| C + Cymoxanil | 10 + 20 | 73 | 67 |
| C + cupric hydroxide | 10 + 55.3 | 33 | 0 |
| C + TPN | 10 + 40 | 33 | 0 |
| C + Propamocarb hydrochloride | 10 + 160 | 33 | 0 |
| C + Cyazofamid | 10 + 9.4 | 33 | 0 |
| C + Metalaxyl | 10 + 10 | 76 | 67 |
| C + Ethaboxam | 10 + 10 | 83 | 67 |
| C + Mancozeb | 10 + 7.5 | 17 | 0 |
| C + Famoxadone | 10 + 10 | 17 | 0 |
| C + Azoxystrobin | 10 + 8 | 17 | 0 |
| C + Benthiavalicarb-isopropyl | 10 + 10 | 92 | 67 |
| C + Metalaxyl M | 10 + 10 | 67 | 17 |
| C + Dimethomorph | 10 + 20 | 33 | 0 |
| Fosetyl-aluminium | 160 | 25 | |
| Cymoxanil | 20 | 67 | |
| cupric hydroxide | 55.3 | 0 | |
| TPN | 40 | 0 | |
| Propamocarb hydrochloride | 160 | 0 | |
| Cyazofamid | 9.4 | 0 | |
| Metalaxyl | 10 | 67 | |
| Ethaboxam | 10 | 67 | |
| Mancozeb | 7.5 | 0 | |
| Famoxadone | 10 | 0 | |
| Azoxystrobin | 8 | 0 | |

TABLE 9-continued

| Effective ingredient in the preparation | Treatment concentration (ppm) | Control value | Theoretical value |
|---|---|---|---|
| Benthiavalicarb-isopropyl | 10 | 67 | |
| Metalaxyl M | 10 | 17 | |
| Dimethomorph | 20 | 0 | |
| A | 10 | 0 | |
| B | 10 | 0 | |
| C | 10 | 0 | |

From the results shown in the above-mentioned Table 9, it could be understood that synergistic effects could be obtained when Compound A, B or C and the compound of Group b are used in combination. Incidentally, even when Compound A, B or C and the compound of Group b are used in combination, no chemical damage symptom was admitted in the plant material, tomato (variety: Ohgata-Fukuju).

Test Example 8

Cucumber Downy Mildew Preventive Test

In a greenhouse, cucumber (variety: Sagamihanpaku) planted in a plastic pot having a diameter of 5 cm was grown to the 3rd to 5th-leaf stage. Spray was carried out in the same manner as in Test example 1, and after drying the chemical liquid, the pots were transferred into a greenhouse. After 3 days from the spray, a sporangium suspension of *Pseudoperonospora cubensis* were inoculated. After inoculation, the pots were placed in a high-humidity chamber (20 to 25° C.), transferred into a greenhouse on the next day, and controlling effects were examined after 7 days from the inoculation. A ratio of lesion area occupied per one leaf of cucumber was determined according to the same index as in Test example 1, and the control value and the theoretical value according to Colby's formula were similarly calculated. The results are shown in Table 10.

TABLE 10

| Effective ingredient in the preparation | Treatment concentration (ppm) | Control value | Theoretical value |
|---|---|---|---|
| A + Fosetyl-aluminium | 10 + 160 | 80 | 68 |
| A + Cymoxanil | 10 + 20 | 80 | 68 |
| A + cupric hydroxide | 10 + 55.3 | 60 | 52 |
| A + TPN | 10 + 40 | 100 | 68 |
| A + Propamocarb hydrochloride | 10 + 160 | 80 | 36 |
| A + Cyazofamid | 10 + 9.4 | 80 | 52 |
| A + Metalaxyl | 10 + 10 | 100 | 68 |
| A + Ethaboxam | 10 + 10 | 80 | 36 |
| A + Mancozeb | 10 + 7.5 | 100 | 68 |
| A + Famoxadone | 10 + 10 | 60 | 4 |
| A + Azoxystrobin | 10 + 8 | 80 | 68 |
| A + Benthiavalicarb-isopropyl | 10 + 10 | 100 | 52 |
| A + Metalaxyl M | 10 + 10 | 100 | 68 |
| A + Dimethomorph | 10 + 20 | 100 | 68 |
| B + Fosetyl-aluminium | 10 + 160 | 92 | 71 |
| B + Cymoxanil | 10 + 20 | 100 | 71 |
| B + cupric hydroxide | 10 + 55.3 | 100 | 57 |
| B + TPN | 10 + 40 | 100 | 71 |
| B + Propamocarb hydrochloride | 10 + 160 | 60 | 42 |
| B + Cyazofamid | 10 + 9.4 | 100 | 57 |
| B + Metalaxyl | 10 + 10 | 100 | 71 |
| B + Ethaboxam | 10 + 10 | 100 | 42 |
| B + Mancozeb | 10 + 7.5 | 100 | 71 |
| B + Famoxadone | 10 + 10 | 100 | 14 |
| B + Azoxystrobin | 10 + 8 | 100 | 71 |
| B + Benthiavalicarb-isopropyl | 10 + 10 | 100 | 57 |
| B + Metalaxyl M | 10 + 10 | 100 | 71 |

TABLE 10-continued

| Effective ingredient in the preparation | Treatment concentration (ppm) | Control value | Theoretical value |
|---|---|---|---|
| B + Dimethomorph | 10 + 20 | 80 | 71 |
| C + Fosetyl-aluminium | 10 + 160 | 95 | 73 |
| C + Cymoxanil | 10 + 20 | 95 | 73 |
| C + cupric hydroxide | 10 + 55.3 | 100 | 60 |
| C + TPN | 10 + 40 | 100 | 73 |
| C + Propamocarb hydrochloride | 10 + 160 | 71 | 46 |
| C + Cyazofamid | 10 + 9.4 | 100 | 60 |
| C + Metalaxyl | 10 + 10 | 100 | 73 |
| C + Ethaboxam | 10 + 10 | 100 | 46 |
| C + Mancozeb | 10 + 7.5 | 100 | 73 |
| C + Famoxadone | 10 + 10 | 100 | 33 |
| C + Azoxystrobin | 10 + 8 | 100 | 73 |
| C + Benthiavalicarb-isopropyl | 10 + 10 | 100 | 60 |
| C + Metalaxyl M | 10 + 10 | 100 | 73 |
| C + Dimethomorph | 10 + 20 | 80 | 73 |
| Fosetyl-aluminium | 160 | 60 | |
| Cymoxanil | 20 | 60 | |
| cupric hydroxide | 55.3 | 40 | |
| TPN | 40 | 60 | |
| Propamocarb hydrochloride | 160 | 20 | |
| Cyazofamid | 9.4 | 40 | |
| Metalaxyl | 10 | 60 | |
| Ethaboxam | 10 | 20 | |
| Mancozeb | 7.5 | 60 | |
| Famoxadone | 10 | 0 | |
| Azoxystrobin | 8 | 60 | |
| Benthiavalicarb-isopropyl | 10 | 40 | |
| Metalaxyl M | 10 | 60 | |
| Dimethomorph | 20 | 60 | |
| A | 10 | 20 | |
| B | 10 | 28 | |
| C | 10 | 33 | |

From the results of the above-mentioned Table 10, it could be understood that synergistic effects could be obtained when Compound A, B or C and the compound of Group b are used in combination. Incidentally, even when Compound A, B or C and the compound of Group b are used in combination, no chemical damage symptom was admitted in the plant material, cucumber (variety: Sagamihanpaku).

Test Example 9

Cucumber Downy Mildew Curative Test

In a greenhouse, cucumber (variety: Sagamihanpaku) planted in a plastic pot having a diameter of 5 cm was grown to the 3rd to 5th-leaf stage. A sporangium suspension of *Pseudoperonospora cubensis* were inoculated, the pots were placed in a high-humidity chamber (20 to 22° C.) and taken out on the next day, and spray was carried out in the same manner as in Test example 1. After drying the chemical liquid, the pots were transferred into a greenhouse, and controlling effects were examined after 7 days from the inoculation. A ratio of lesion area occupied per one leaf of cucumber was determined according to the same index as in Test example 1, and the control value and the theoretical value according to Colby's formula were similarly calculated. Thr results are shown in Table 11.

TABLE 11

| Effective ingredient in the preparation | Treatment concentration (ppm) | Control value | Theoretical value |
|---|---|---|---|
| A + Fosetyl-aluminium | 10 + 160 | 92 | 72 |
| A + Cymoxanil | 10 + 20 | 73 | 72 |

TABLE 11-continued

| Effective ingredient in the preparation | Treatment concentration (ppm) | Control value | Theoretical value |
|---|---|---|---|
| A + cupric hydroxide | 10 + 55.3 | 92 | 58 |
| A + TPN | 10 + 40 | 93 | 86 |
| A + Propamocarb hydrochloride | 10 + 160 | 92 | 17 |
| A + Cyazofamid | 10 + 9.4 | 78 | 72 |
| A + Metalaxyl | 10 + 10 | 100 | 93 |
| A + Ethaboxam | 10 + 10 | 83 | 72 |
| A + Mancozeb | 10 + 7.5 | 87 | 72 |
| A + Famoxadone | 10 + 10 | 100 | 93 |
| A + Azoxystrobin | 10 + 8 | 100 | 93 |
| A + Benthiavalicarb-isopropyl | 10 + 10 | 92 | 72 |
| A + Metalaxyl M | 10 + 10 | 100 | 86 |
| A + Dimethomorph | 10 + 20 | 75 | 58 |
| B + Fosetyl-aluminium | 10 + 160 | 92 | 78 |
| B + Cymoxanil | 10 + 20 | 92 | 78 |
| B + cupric hydroxide | 10 + 55.3 | 97 | 67 |
| B + TPN | 10 + 40 | 97 | 89 |
| B + Propamocarb hydrochloride | 10 + 160 | 100 | 33 |
| B + Cyazofamid | 10 + 9.4 | 93 | 78 |
| B + Metalaxyl | 10 + 10 | 100 | 94 |
| B + Ethaboxam | 10 + 10 | 93 | 78 |
| B + Mancozeb | 10 + 7.5 | 87 | 78 |
| B + Famoxadone | 10 + 10 | 100 | 94 |
| B + Azoxystrobin | 10 + 8 | 100 | 94 |
| B + Benthiavalicarb-isopropyl | 10 + 10 | 100 | 78 |
| B + Metalaxyl M | 10 + 10 | 100 | 89 |
| B + Dimethomorph | 10 + 20 | 100 | 67 |
| C + Fosetyl-aluminium | 10 + 160 | 93 | 78 |
| C + Cymoxanil | 10 + 20 | 92 | 78 |
| C + cupric hydroxide | 10 + 55.3 | 97 | 67 |
| C + TPN | 10 + 40 | 97 | 89 |
| C + Propamocarb hydrochloride | 10 + 160 | 100 | 33 |
| C + Cyazofamid | 10 + 9.4 | 93 | 78 |
| C + Metalaxyl | 10 + 10 | 100 | 94 |
| C + Ethaboxam | 10 + 10 | 93 | 78 |
| C + Mancozeb | 10 + 7.5 | 87 | 78 |
| C + Famoxadone | 10 + 10 | 100 | 94 |
| C + Azoxystrobin | 10 + 8 | 100 | 94 |
| C + Benthiavalicarb-isopropyl | 10 + 10 | 100 | 78 |
| C + Metalaxyl M | 10 + 10 | 100 | 89 |
| C + Dimethomorph | 10 + 20 | 100 | 67 |
| Fosetyl-aluminium | 160 | 67 | |
| Cymoxanil | 20 | 67 | |
| cupric hydroxide | 55.3 | 50 | |
| TPN | 40 | 83 | |
| Propamocarb hydrochloride | 160 | 0 | |
| Cyazofamid | 9.4 | 67 | |
| Metalaxyl | 10 | 92 | |
| Ethaboxam | 10 | 67 | |
| Mancozeb | 7.5 | 67 | |
| Famoxadone | 10 | 92 | |
| Azoxystrobin | 8 | 92 | |
| Benthiavalicarb-isopropyl | 10 | 67 | |
| Metalaxyl M | 10 | 83 | |
| Dimethomorph | 20 | 50 | |
| A | 10 | 17 | |
| B | 10 | 33 | |
| C | 10 | 33 | |

From the results shown in the above-mentioned Table 11, it could be understood that synergistic effects could be obtained when Compound A, B or C and the compound of Group b are used in combination. Incidentally, even when Compound A, B or C and the compound of Group b are used in combination, no symptom of chemical damage was admitted in the plant material, cucumber (variety: Sagamihanpaku).

UTILIZABILITY IN INDUSTRY

The plant disease control composition of the present invention showed a broad spectrum against various plant pathogens (for example, rice blast (*Pyricularia oryzae*), and gray mold (*Botrytis cinerea*) of tomato, cucumber and kidney bean, etc.) including fungi and bacteria resistant to chemicals, and shows excellent controlling effects (synergistic controlling effects) which could never be expected from a single component alone. Also, it shows high plant disease controlling effects against existing fungi and bacteria resistant to chemicals, and no chemical damage against plants can be admitted so that it can be used as an excellent plant disease controlling agent.

The invention claimed is:

1. A plant disease control composition comprising
(Group a)
(a) at least one quinoline compound selected from the group consisting of
(a-14) 3-(5-fluoro-3,3,4,4-tetramethyl-3,4-dihydroisoquinolin-1-yl)quinoline,
(a-18) 3-(4,4-difluoro-3,3-dimethyl-3,4-dihydroisoquinolin-1-yl)quinoline, and
(a-20) 3-(4,4,5-trifluoro-3,3-dimethyl-3,4-dihydroisoquinolin-1-yl)quinoline,
or a salt thereof, and
(Group b)
(b) one or more fungicides selected from the group consisting of:
(b-4-1) Penthiopyrad,
(b-4-3) Furametpyr,
(b-4-4) Boscalid,
(b-4-5) Fenhexamid,
(b-4-6) Cyflufenamid,
(b-4-8) Mandipropamid,
(b-4-9) Bixafen,
(b-4-10) Carboxin,
(b-4-14) Thifluzamide,
(b-4-16) Ethaboxam,
(b-4-17) Zoxamide,
(b-4-18) Tiadinil,
(b-4-19) Isotianil,
(b-4-22) Fluopicolide,
(b-4-23) Fluopyram,
(b-4-26) Penflufen,
(b-4-27) Sedaxane, and
(b-4-28) Isopyrazam,
as effective ingredients.

2. A controlling method for controlling plant diseases comprising applying the plant disease control composition according to claim 1.

3. A method for controlling plant diseases, which comprises
applying a compound of Group a and a compound of Group b at the same time, or applying either a compound of Group a or Group b, and then applying the other compound of Group a or Group b sequentially, wherein Group a is at least one quinoline compound selected from the group consisting of:
(a-14) 3-(5-fluoro-3,3,4,4-tetramethyl-3,4-dihydroisoquinolin-1-yl)quinoline,
(a-18) 3-(4,4-difluoro-3,3-dimethyl-3,4-dihydroisoquinolin-1-yl)quinoline, and
(a-20) 3-(4,4,5-trifluoro-3,3-dimethyl-3,4-dihydroisoquinolin-1-yl)quinoline,
or a salt thereof, and
Group b is one or more fungicides selected from the group consisting of:
(b-4-1) Penthiopyrad,
(b-4-3) Furametpyr,
(b-4-4) Boscalid,
(b-4-5) Fenhexamid,
(b-4-6) Cyflufenamid,
(b-4-8) Mandipropamid,
(b-4-9) Bixafen,
(b-4-10) Carboxin,
(b-4-14) Thifluzamide,
(b-4-16) Ethaboxam,
(b-4-17) Zoxamide,
(b-4-18) Tiadinil,
(b-4-19) Isotianil,
(b-4-22) Fluopicolide,
(b-4-23) Fluopyram,
(b-4-26) Penflufen,
(b-4-27) Sedaxane, and
(b-4-28) Isopyrazam.

* * * * *